(12) United States Patent
Pancholi et al.

(10) Patent No.: US 6,190,659 B1
(45) Date of Patent: Feb. 20, 2001

(54) BACTERIAL PLASMIN BINDING PROTEIN AND METHODS OF USE THEREOF

(75) Inventors: Vijaykumar Pancholi, New York; Vincent A. Fischetti, West Hempstead, both of NY (US)

(73) Assignee: The Rockefeller University, New York, NY (US)

(*) Notice: Under 35 U.S.C. 154(b), the term of this patent shall be extended for 0 days.

(21) Appl. No.: 08/715,034

(22) Filed: Sep. 17, 1996

(51) Int. Cl.⁷ .......................... A61K 38/48; A61K 39/02; C12N 11/00; C07K 1/00
(52) U.S. Cl. .................................. 424/94.63; 424/190.1; 424/192.1; 424/234.1; 424/244.1; 424/282.1; 435/174; 435/183; 435/212; 435/215; 435/216; 435/217; 435/220; 514/2; 530/300; 530/350; 530/403; 530/810; 530/825
(58) Field of Search .................................. 530/350, 825, 530/403, 412, 810, 300; 424/244.1, 234.1, 282.1, 94.1, 94.63, 190.1, 192.1; 514/2; 435/174, 183, 212, 215, 216, 217, 220

(56) References Cited

U.S. PATENT DOCUMENTS

| 4,879,213 | * | 11/1989 | Fox et al. . |
| 5,237,050 | | 8/1993 | Boyle et al. . |
| 5,328,996 | | 7/1994 | Boyle et al. . |
| 5,580,563 | * | 12/1996 | Tani . |

OTHER PUBLICATIONS

Beachey EH et al.,*J. Exp. Med*, 150:862–77 (1979).
Fox En et al., *J. Clin. Invest,*52: 1885–92, (1973).
Lopez–Alemany, R. et al (1994), Thrombosis Research 75:371–381.
Lottenberg et al., (1987), Infection and Immunity, 55;1914–1918.
Lottenberg et al (1992) J. Bacteriol. 174: 5204–5210.
Miles, L.A. (1991) Biochemistry 30,1682–1691.
Pancholi et al. (1988) J.Bacteriol.. 170:2618.
Pancholi et al. (1989) J.Exp.Med. 170: 2119.
Pancholi, V. and Fischetti, V.A. (1992), J.Exp.Med. 176: 415–426.
Redlitz et al, (1995)Eur. J. Biochem. 227:407–415.
Berge et al (Journal of Biological Chemistry 268(34) pp25417–25424, Dec. 5, 1993.*
Kaufmann et al. Caries Research 1992 vol. 26(2), 110–116 Abstract only.*
Leyva–Vazques et al. J. Bacteriol. 1994, vol. 176, No. 13, 3903–3910.*
Lazar et al. Mol. & Cell. Biol. 1988 vol. 8, No. 3, 1247–1252.*
Burgess et al. J. Cell. Biol. 1990 vol. 111, 2129–2138.*
Ellis, R.W. in Vaccines, Plotkin et al. ed., published by W.B. Saunders Co. Philadelphia 1988, 571.*
Maggio, Enzyme–Immunoassay 1987, CRC Press, Inc., Boca Raton, Florida, 168–169.*
Harlow et al Antibodies A Laboratory Manual Cold Spring Harbor Laboratory 1988, 285, 287.*

* cited by examiner

Primary Examiner—Mark Navarro
(74) Attorney, Agent, or Firm—Klauber & Jackson

(57) ABSTRACT

The present invention describes a novel polypeptide, and methods of its use in effective thrombolytic therapy in the treatment of coronary and pulmonary thrombosis. Its use is also disclosed in vaccines to abrogate a streptococcal infection. Pharmaceutical compositions containing the novel polypeptide are included. One particular form of the novel polypeptide is streptococcal surface enolase (SEN), a specific binding protein for human plasmin and/or human plasminogen on group A streptococci that displays classical α-enolase activity, i.e., it can catalyze the dehydration of D-glycerate-2-phosphate to phosphoenolpyruvate. In addition, SEN impedes the inhibition of the fibrinolytic activity of plasmin by $\alpha_2$-antiplasmin and can bind plasminogen without preventing streptokinase from cleaving this plasmin precursor.

21 Claims, 12 Drawing Sheets

Coomassie Stain

Autoradiograph
($I^{125}$- Plasminogen)

Coomassie Stain

Autoradiograph
($I^{125}$- Plasmin)

N-terminal amino acid microsequencing:

```
                   1                                                50
Intact Molecule: SIITDVYAREVLDSRGNPTLEVEVYTESGAFGRGMVPSGAGTTEHEAVEL
                  ::::::::::::::::::::: :::::::::  ::  :: ::::::::
B.subtilis:      IVDVYAREVLDSRGNPTVEVEVYTETGAFGRALVPSGASTGQYEAVEL
α-enolase Internal                        ERGLVTAVGDEGGFA
Sequence-1:                     ::::: :::::::::             215
                   193    VLSAKGLNTAVGDEGGFAPNLGS
B.subtilis
α-enolase
(Location-Middle of the molecule)

Internal Sequence-2:          SAAGYTAVVSH
(Mol mass 3367.1)       355   ::::: ::      370
B.subtilis α-enolase    EMAKRAGYTAVISHRS
(Location- towards the C-terminus)
```

FIG. 3

CHARACTERIZATION OF THE 45 kDA PLASMIN (OGEN) - BINDING PROTIEN

PREVALENCE OF 'SEN' IN VARIOUS M TYPES OF GROUP A STREPTOCOCCI AND STREPTOCOCCAL GROUPS

Polyclonal anti-SEN antibodies were raised in rabbits and affinity purified on SEN and Protien A affinity columns. Cell wall extracts from various M types (lysin extracts) and those from several streptococcal groups (mutanolysin extracts) were examined for the presence of SEN using this antibody.

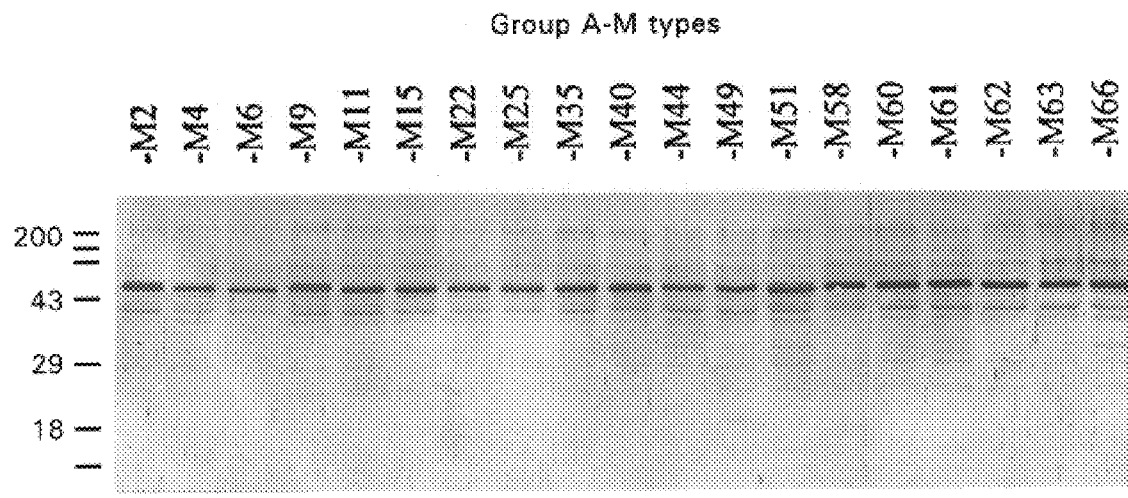

FIG. 9A

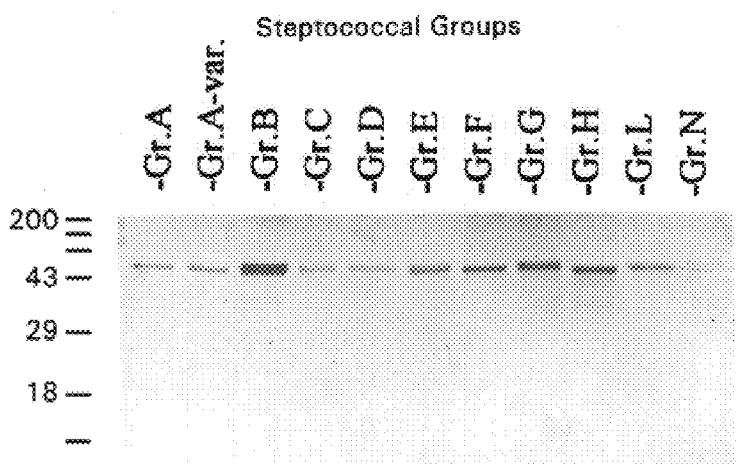

FIG. 9B

BACTERIAL PLASMIN BINDING PROTEIN AND METHODS OF USE THEREOF

GOVERNMENTAL SUPPORT

The research leading to the present invention was supported, at least in part, by a Public Health Service Grant, No. A2 11822. Accordingly, the Government may have certain rights in the invention.

FIELD OF THE INVENTION

The present invention discloses an isolated bacterial protein that specifically binds to plasmin. This association stabilizes plasmin by hindering the inhibition of plasmin by $\alpha_2$-antiplasmin. Plasminogen bound to the isolated bacterial protein is readily activated by streptokinase or other tissue plasminogen activators as compared to the equal amount of free plasminogen. Generation of antibodies to this novel protein in an animal protects the animal against pathogenic streptococci infection. Methods of exploiting these properties of the protein and its antibodies are included.

BACKGROUND OF THE INVENTION

Plasminogen activators convert plasminogen to the active form of the enzyme, plasmin, which catalyzes the digestion of fibrin clots. Plasminogen activators such as streptokinase and tissue plasminogen activator (TPA) have been approved by the Food and Drug Administration for thrombolytic therapy in the treatment of coronary and pulmonary thrombosis. These proteases may also be used in the solubilization of fibrin clots formed when catheters or shunts are in place for long periods of time. The use of plasminogen activators has saved countless lives through activating plasmin, which in turn, dissolves artery-clogging blood clots.

On the other hand, the presence of active plasmin in the serum for long periods of time or the accumulation of active plasmin can lead to serious consequences, such as uncontrolled bleeding. Thus, the use of plasminogen activators are not without side effects. Due to the requirement of the relatively large quantities of plasminogen activator for effective therapy and the resulting generalized lytic state of the serum, the patient is always at risk of bleeding. This risk is lower with TPA, because of the specific fibrin binding activity of this enzyme. However, because of the relatively high doses required to treat coronary artery thrombosis, bleeding still occurs in a number of patients. In addition, in the case of coronary artery thrombosis, re-occlusion of the blood vessel following successful clot lysis occurs in a number of patients. Furthermore, TPA has been shown to have a relatively short half life in vivo. This is a particular problem since blood plasma naturally contains a potent inhibitor of plasmin, $\alpha_2$-antiplasmin, which can counteract the life-saving ability of TPA, if TPA is administered at lower doses. Finally, TPA is very expensive and some Healthcare providers will not authorize the use of the TPA in lieu of its less-specific analogs because of financial concerns.

Recently, a plasmin binding molecule from the surface of an untypable clinical strain of group A streptococci has been reported [Lottenberg et al (1992) J. Bacteriol. 174: 5204–5210, See also U.S. Pat. No. 5,237,050 dated Aug. 17, 1993 and its continuation U.S. Pat. No. 5,328,996, dated Jul. 12, 1994]. This protein is structurally similar to glyceraldehyde-3-phosphate dehydrogenase (GAPDH). This protein has been described as having plasmin-binding activity and could possibly be administered to increase fibrolytic activity. A novel 35.8 kDa multifunctional protein on the surface of group A streptococci has also been reported. This protein (streptococcal surface dehydrogenase, SDH) was also found to be structurally and functionally related to GAPDH [Pancholi, V. and Fischetti, V. A. (1992), J.Exp.Med. 176: 415–426]. In contrast to the finding of Lottenberg et al (see supra), however, SDH was found to bind very weakly to plasmin and plasminogen.

On the other hand, a molecule having homology with $\alpha$-enolase recently has been described to be a plasmin receptor on human carcinoma cells [Lopez-Alemany, R. et al (1994), Thrombosis Research 75:371–381]. Enolase is a 2-phospho-D-glycerate hydrolase (hydrolyase) (E.C. 4.2.1.11), that catalyzes the dehydration of D-glycerate-2-phosphate to yield enolpyruvate phosphate (phosphoenolpyruvate). Three classes of isoenzymes have been identified in mammalian tissues. Each enzyme is a homodimeric protein composed of two $\alpha$, $\beta$, or $\gamma$ subunits [Zommzely-Neurath, C. E., 1983 in Hand book of Neurochemistry, ed Lajtha, A. (Plenum Press New York), 2nd ed, vol 4, pp. 403–433]. Isoenzyme $\alpha$ is present in most tissue, $\beta$ is localized in muscle tissue and $\gamma$ is found only in nervous tissue. Although, enolase has been generally found in the cytosol, Miles and his group recently reported that the $\alpha$-isoform of enolase is a candidate for being a plasminogen receptor on U937 monocytoid cells [Miles, L. A. (1991) Biochemistry 30,1682–1691], and also for being on the surfaces of peripheral blood monocytes and neutrophils [Redlitz et al, (1995) Eur. J. Biochem. 227:407–415]. However, enolase has never been identified on the surface of bacteria.

Group A streptococci (*Streptococcus pyogenes*) are the causative agent for many suppurative infections in humans, most notably pharyngitis, impetigo, scarlet fever and more recently, invasive disease such as necrotizing fascitis. The Centers for Disease Control estimate that >35 million cases of pharyngitis occur in the U.S. each year. The incidence of group A streptococcal respiratory infection rises sharply at age four, peaks at age six, and declines above age ten, reaching adult levels by 18 years [Fischetti et al.,*J.Exp.Med*, 133:1105–1117(1971)]. At its peak incidence, as many as 50% of children between the age of five and seven suffer from streptococcal infection each year. Approximately 3–5% of individuals with untreated or inadequately treated streptococcal pharyngitis may develop acute rheumatic fever (Fischetti, 1971, supra). Although antibiotic treatment (primarily penicillin) has reduced the overall frequency of rheumatic fever in the U.S., several outbreaks have been reported in Utah [Veasey et al.,*N.Engl J Med*, 316:421–7 (1987)],[Veasey L G et al., *J.Pediatr*,Jan. 9–16 , 1994] Pennsylvania [Wald E R et al.,*Pediatrics*, 80:371–4(1987)], and Ohio [Congeni, B. et al.,*J. Pediatr*,111:176–99 (1987)]. The recent appearance of streptococcal-associated toxic shock syndrome, and severe tissue necrosis may be indicative of increased or altered virulence of certain strains [Stevens D L et al., *N. Engl.J.Med.*, 321:1–7 (1989)]. No effective vaccine for group A streptococci is available despite more than 50 years of continuous effort. This may in part be due the finding that only type-specific antibodies to the surface M protein are opsonic, and >80 different serotypes of M protein have been identified. Early attempts at vaccine development have resulted in only type-specific protection [Fox En et al.,*J. Clin Invest*, 52:1885–92, (1973)] [Beachey E H et al., *J. Exp. Med*, 150:862–77 (1979).

Thus, agents that can be used in combination with plasminogen activators to improve their specific therapeutic action while diminishing their side effects are needed.

Similarly, agents that can lower the cost of thrombolytic therapy by lowering the amount of TPA required are also needed.

In addition, methods for immunizing people against pathogenic group A streptococci are needed.

The citation of any reference herein should not be construed as an admission that such reference is available as "Prior Art" to the instant application.

SUMMARY OF THE INVENTION

The present invention describes a novel polypeptide, along with methods of its use both in effective thrombolytic therapy, as well as in vaccines to abrogate a streptococcal infection. In one embodiment, the polypeptide is streptococcal surface enolase (SEN), a specific binding protein for human plasmin and/or human plasminogen on group A streptococci. As disclosed herein, SEN is identified, purified, and characterized as to its physical and functional qualities. SEN has been found to bind with a very high affinity to plasminogen and plasmin (see FIG. 11). Thus, in one aspect of the invention the plasmin binding protein is a therapeutic agent in treatments to achieve or prolong fibrinolytic activity.

In another aspect of the invention the plasmin binding protein can be used in a vaccine to abrogate a streptococcal infection, or to generate antibodies for passive immunotherapy. In one such embodiment, affinity purified polyclonal anti-plasmin binding protein antibodies are used to enhance phagocytosis of a group A streptococcal strain of bacteria.

In its broadest form, the present invention describes an isolated plasmin binding protein that is a polypeptide having the following characteristics: (i) it is naturally found on the surface of a bacterium; (ii) it possesses a binding affinity for plasmin; (iii) when purified it has a molecular weight of 45 kDa determined by SDS-PAGE under reducing conditions; and (iv) is a homologue of the protein having the N-terminal amino acid of SEQ ID NO: 1. Preferably,it has a N-terminal amino acid sequence that has at least 80% sequence homology with that of SEQ ID NO: 1. In a more preferred embodiment, the N-terminal amino acid sequence has at least 90% sequence homology with that of SEQ ID NO: 1. In an even more preferred embodiments the N-terminal amino acid sequence has at least 95% sequence homology with that of SEQ ID NO: 1. In the most preferred embodiment the N-terminal amino acid sequence is that of SEQ ID NO: 1. In one particular embodiment the plasmin binding protein is SEN, an isolated polypeptide naturally found on the surface of group A streptococci bacteria.

In preferred embodiments, the plasmin binding protein is a polypeptide that has one or more of the following additional characteristics: (i) when bound to plasmin it impedes the inhibition of the fibrinolytic activity of plasmin by $\alpha_2$-antiplasmin; (ii) it can bind plasminogen without preventing streptokinase from cleaving this precursor protein to active plasmin; and (iii) it can catalyze the dehydration of D-glycerate-2-phosphate to phosphoenolpyruvate under standard conditions for enolase assays (Bergmeyer, H. (ed) (1973). Methods of Enzymatic Analysis. Verleg Chemie, Weinheim (FRG)). In the most preferred embodiment, the polypeptide has all of these additional characteristics. In yet another embodiment of the present invention plasminogen bound to the plasmin binding protein causes an enhancement of the ability of a plasminogen activator to convert the precursor protein to active plasmin.

The present invention also includes compositions comprising the isolated polypeptide of the present invention bound to plasmin and/or with plasminogen. In another embodiment of the invention, a composition comprises the isolated polypeptide associated with an anti-fibrin antibody.

The present invention also includes pharmaceutical compositions. One embodiment comprises the isolated polypeptide and a pharmaceutically acceptable carrier. In a preferred embodiment the isolated polypeptide is attached to a solid phase support conjugated to a polymer (such as polyethylene glycol) or encased in a bio-degradeable or an inert polymer matrix, among other possible delivery means.

In another embodiment the pharmaceutical composition further comprises a plasminogen activator. In a preferred embodiment of this type, the plasminogen activator is tissue plasminogen activator either alone or in combination with other similar plasminogen activators. In other embodiments, the plasminogen activator can be streptokinase alone, urokinase alone, or mixtures of either one or both of these two with other suitable plasminogen activators, including tissue plasminogen activator. Any person with skill in the art would know of other similar, suitable plasminogen activators.

In another embodiment a pharmaceutical composition comprises the isolated polypeptide of the present invention bound to plasmin and a pharmaceutically acceptable carrier. In yet another embodiment, a pharmaceutical composition comprises the composition of the isolated polypeptide of the present invention bound to plasminogen and a pharmaceutically acceptable carrier. Further embodiments of this pharmaceutical composition can also include a plasminogen activator as described above.

In still another embodiment, a pharmaceutical composition comprises the isolated polypeptide of the present invention associated with an anti-fibrin antibody and a pharmaceutically acceptable carrier. Further embodiments of this pharmaceutical composition can also include a plasminogen activator as described above and/or plasmin.

The present invention also includes nucleic acids that encode the isolated polypeptide of the present invention. In one embodiment, the nucleic acid is an RNA. In another embodiment of this type, the nucleic acid is DNA. In a preferred embodiment, the DNA is a cDNA. In addition, expression vectors comprising the DNA of the present invention operatively linked to an expression control sequence are also included in the present invention.

The present invention also comprises antibodies to the plasmin binding protein. In one embodiment the antibody is a polyclonal antibody. In another embodiment the antibody is a monoclonal antibody. In a related embodiment, the present invention includes an immortal cell line that produces a monoclonal antibody to the plasmin binding protein of the present invention. In preferred embodiment, the antibody is a chimeric antibody. All of these antibodies may be labeled as described herein.

A related aspect of the present invention includes a method for generating antibodies in an animal, comprising administering an antibody-generating amount of the isolated polypeptide of the present invention, or immunogenic fragments together with a non-toxic adjuvant.

The present invention includes methods for effective thrombolytic therapy. In one embodiment of the present invention, the method comprises administering to an animal a therapeutically effective amount of a pharmaceutical composition comprising the plasmin binding protein and a pharmaceutically acceptable carrier. In alternative embodiments the method comprises administering to an animal a therapeutically effective amount of a pharmaceutical composition comprising the isolated polypeptide of the present invention attached to a solid phase support along with a pharmaceutically acceptable carrier. In another embodiment the pharmaceutical composition further comprises a plasminogen activator. The plasminogen activator can be the tissue plasminogen activator, streptokinase, urokinase, other suitable plasminogen activators and mixtures thereof.

In yet another embodiment, the method comprises administering to an animal a therapeutically effective amount of a pharmaceutical composition comprising the isolated polypeptide of the present invention bound to plasmin and a pharmaceutically acceptable carrier. In a related method, the pharmaceutical composition comprises the composition of the isolated polypeptide of the present invention bound with plasminogen and a pharmaceutically acceptable carrier. Further embodiments of this pharmaceutical composition can also include a plasminogen activator as described above.

In still another embodiment, the method comprises administering to an animal a therapeutically effective amount of a pharmaceutical composition that comprises the isolated polypeptide of the present invention associated with an anti-fibrin antibody and a pharmaceutically acceptable carrier. Further embodiments of this pharmaceutical composition can also include a plasminogen activator as described above and/or plasmin. In preferred embodiments of all of the methods for effective thrombolytic therapy the animal is a human.

Another aspect of the invention include methods of making a recombinant the plasmin binding protein comprising by placing an expression vector containing a nucleic acid of the present invention into a suitable host cell. In one such embodiment the host cell is an E. coli. In another embodiment, the host cell is a yeast cell. In yet a third embodiment the host cell is an insect cell. The present invention also includes the isolation of said recombinant polypeptide and the recombinant polypeptide produced by these methods.

The present invention includes methods for generating antibodies in an animal, comprising administering to the animal an antibody-generating amount of the plasmin binding protein of the present invention together with a non-toxic adjuvant. In a related aspect of the present invention vaccines for use in the prevention of streptococcal infection in an animal are included. One such embodiment comprises the isolated polypeptide of the present invention, together with a non-toxic adjuvant. In a related embodiment, the vaccine comprises an immunogenic fragment of the plasmin binding protein as described above, together with a non-toxic adjuvant. In one embodiment of this type, the fragment is obtained from a portion of the isolated polypeptide that does not bind to monoclonal antibodies which inhibit the enolase activity. In another embodiment, the immunogenic fragment has amino acid sequences contained in SEQ ID NO: 1. In preferred embodiments the antibodies are protective.

The present invention also includes methods for protecting or treating an animal for/from streptococcal infection that comprises administering an amount of an antibody raised against the isolated polypeptide of the present invention to the animal effective to induce opsonization of streptococcal bacteria present in the animal.

These and other aspects of the present invention will be better appreciated by reference to the following drawings and Detailed Description.

BRIEF DESCRIPTION OF THE DRAWING

FIG. 2A. 60% Ammonium sulfate cut prior to placing on the column, the two column washes (F.T.1 and F.T.2) and the resulting numbered elution fractions were resolved by 12% SDS-PAGE under reducing conditions and labeled with Coomassie Blue. FIG. 2B. As in FIG. 2A except the SDS-PAGE was further subjected to Western Blot analysis on a PVDF membrane and resolved by autoradiography with the use of $^{125}$I-plasminogen as the probe.

FIG. 3: Microsequencing of the isolated plasmin binding protein. Portions of the amino acid sequence of the 45 kDa plasmin binding protein was determined as described in Example 1 and compared to B. subtilus α-enolase as shown. Internal Sequence-1 is peptide-2 and Internal Sequence-2 is peptide-3.

FIGS. 9A–9B: Prevalence of the plasmin binding protein in various M types of group A streptococcal groups. Polyclonal anti-SEN antibodies were raised in rabbits and affinity purified on SEN and Protein A affinity columns as described in Example 1. Cell walls from assorted streptococci bacteria were examined for the presence of SEN using the antibody. The proteins were resolved on 12% SDS-PAGE under reducing conditions, Western blotted and reacted with the antibodies. FIG. 9A depicts cell wall extracts from various M types (lysin extracts). FIG. 9B depicts cell walls from several streptococcal groups (mutanolysin extracts).

DETAILED DESCRIPTION OF THE INVENTION

Figure 1A:
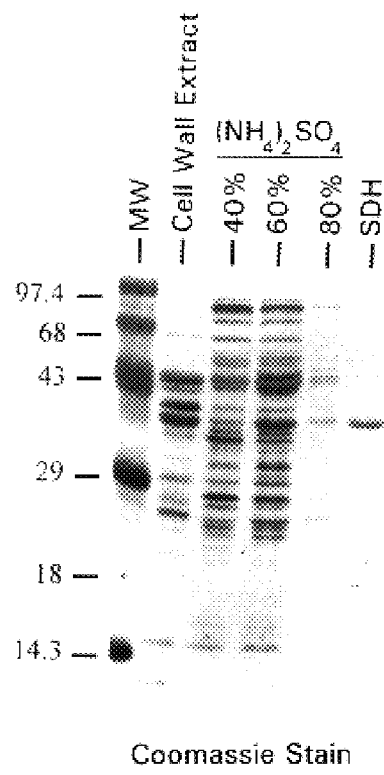
FIGS. 1A–1D. Identification of a novel plasmin(ogen)-binding protein. Streptococcal cell wall extracts were fractionated by sequential ammonium sulfate saturation (0–40%, 40–60% and 60–80%). Proteins in the resulting fractions were resolved by 12% SDS-PAGE under reducing conditions (FIGS. 1A and 1C); and by Western blots on a PVDF membrane using autoradiography and $^{125}$I-plasminogen (FIG. 1B) and $^{125}$I-plasmin (FIG. 1D) as probes. Lane 1: standard molecular weight markers; Lane 2: the cell wall extract prior ro ammonium sulfate fractionation; Lane 3: fraction from 40% ammonium sulfate saturation cut; Lane 4: fraction from 60% ammonium sulfate saturation cut; Lane 5: fraction from 80% ammonium sulfate saturation cut; Lane 6: purified streptococcal surface dehydrogenase (SDH).
Figure 1B:
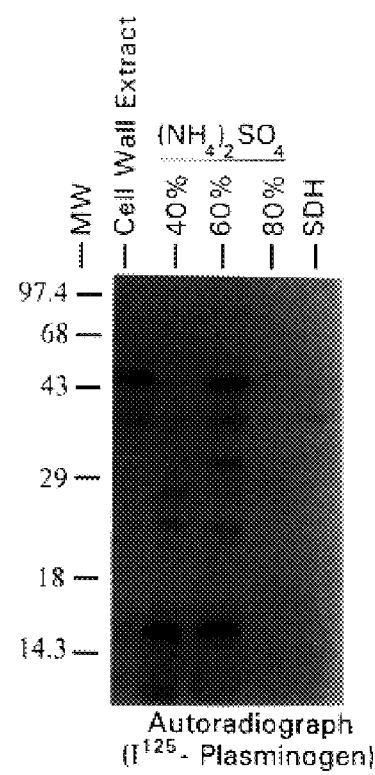
Figure 1C:
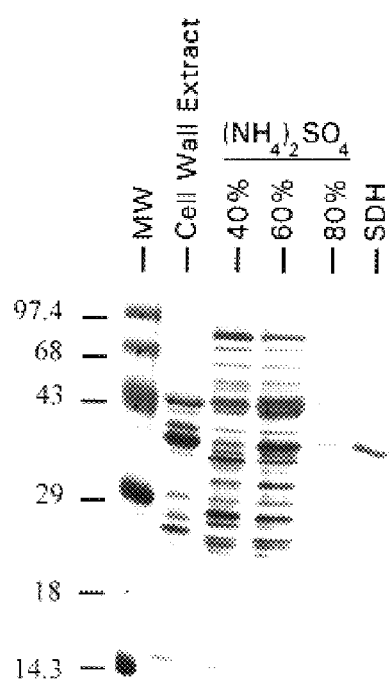
Figure 1D:
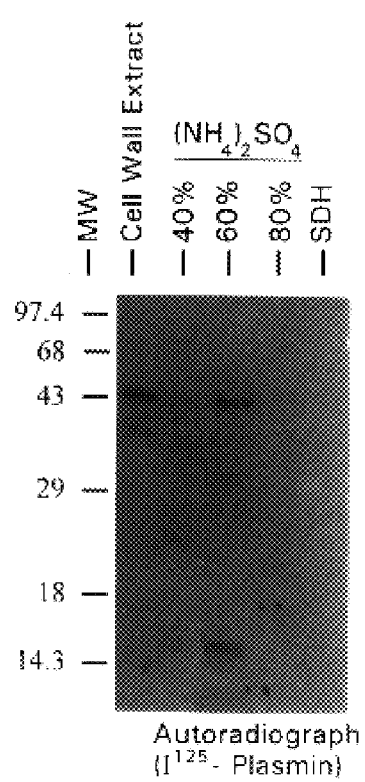

As described herein, a novel plasmin binding protein (45 kDa) has been isolated from the surface of streptococci, which is surprisingly similar to α-enolase, an important glycolytic enzyme generally found in the cytoplasm. The plasmin binding protein retains its enolase activity while bound on the surface of group A streptococci, and is therefore named SEN (streptococcal surface enolase). SEN is distinct from the 48 kDa streptokinase and the 35.8 kDa SDH (39 kDa as determined by SDS-PAGE, Pancholi and Fischetti (1992) see supra) and the 41 kDa Plr (Lottenberg et al (1992), see supra) proteins reported previously.

As used herein the "plasmin binding protein" and the "isolated polypeptide" of the present invention are used interchangeably and represent the isolated protein having the following characteristics: (i) it is naturally found on the surface of a bacterium, particularly streptococci, and more particularly Group A streptococci; (ii) it possesses a binding affinity for plasmin; (iii) when purified it has a molecular weight of about 45 kDa determined by SDS-PAGE under reducing conditions; and (iv) it is a homologue or allelic variant of SEN having a N-terminal amino acid sequence shown in SEQ ID NO: 1. SEN is one specific form of the plasmin binding protein.

As used herein the term "associates" or "associated" are used generally and are meant to include all such specific interactions that result in two or more molecules showing a preference for one another relative to some third molecule. This includes processes such as covalent linkages, ionic, hydrophobic and hydrogen bonding but does not include non-specific associations such as solvent preferences.

One key property of the plasmin binding protein of the present invention is that the fibrinolytic activity of plasmin bound to the plasmin binding protein is not suppressed by the natural plasmin inhibitor, $\alpha_2$-antiplasmin. Thus, one utility for the plasmin binding protein is its use in combination with the available plasminogen activators to prolong their activity in vivo. Such use dramatically enhances the effective activity of these agents since the amount of the plasminogen activators needed to be administered to achieve a desired fibrinolytic activity can be reduced when the plasmin binding protein is co-administered. Co-administration of the plasma binding protein advantageously minimizes the side-effects of the plasminogen activators, which currently are required to be administered in relatively high doses to overcome the relatively short half-life of their effect. Therefore, the plasmin binding protein of the present invention, alone, or as a plasmin—plasmin binding protein complex, or further in conjunction with the administration of a minimal amount of a plasminogen activators such as streptokinase, urokinase, or TPA, can be employed as the effective treatment for preventing re-occlusion of blood vessels. Such treatments can also minimize the risk of plasminogen activator-mediated bleeding.

In a specific embodiment, a derivative or analog of the plasmin binding protein is functionally active, i.e., capable of exhibiting one or more functional activities associated with a full-length, wild-type plasmin binding protein of the invention, such as binding plasmin and protecting it from $\alpha_2$-antiplasmin inhibition. In second embodiment, a plasmin binding protein of the invention can be prepared by adding a fibrin binding domain(s) from an anti-fibrin antibody. In still a third embodiment, a derivative is prepared that retains its plasmin protecting capacity, plus has an added catalytic domain from a plasminogen activator, such as TPA, and thereby is also capable of converting the plasminogen precursor to active plasmin. In yet another embodiment, a plasmin binding protein of the invention can be prepared by adding the catalytic domain of plasmin thereby forming a plasmin/plasmin binding protein chimera that is covalently linked through a dipeptide bond.

Another aspect of the present invention relates to the use of the plasmin binding protein as a vaccine, since the affinity purified polyclonal anti-plasmin binding protein antibodies are found to be opsonic, i.e., in the presence of these specific antibodies, phagocytosis of group A streptococcal strain is significantly enhanced. The explanation for this result is that Group A streptococci or other related streptococci which have the plasmin binding protein on their surfaces, use the plasmin binding property to advantageously spread through the tissues of a host animal. Thus, a specific immune response against the plasmin binding protein can be used to abrogate such a streptococcal infection.

Purification and Characterization of the Plasmin Binding Protein

Characteristics of the Plasmin Binding Protein.

The bacterial plasmin binding protein of the present invention has an enolase-like catalytic activity and may be obtained from gram positive bacterial cell walls. In one preferred embodiment, the plasmin binding protein is obtained from streptococcal bacteria. In more preferred embodiments, the plasmin binding protein is obtained from the cell walls of Groups A,B,C,D,E,F,G,H,L, and M serotypes of streptococcal bacteria (see FIG. 9). In the most preferred embodiment, the plasmin binding protein is obtained from the cell wall of an M serotype of streptococcal bacterium.

The plasmin binding protein has sequence similarities with α-enolases and, as mentioned above, has a catalytic activity similar to this glycolytic protein. In some embodiments, the sequence similarity is greater than 50%. In preferred embodiments, the sequence similarity is greater than 80%. In one particular embodiment, an N-terminal sequence consisting of about 50 amino acids of the plasmin binding protein has more than 90% sequence similarity with the corresponding N-terminal end of streptococcal α-enolase.

The molecular weight of the plasmin binding protein for one particular embodiment of the present invention has been determined to be approximately 45 kDa by SDS-PAGE. The catalytic activity of the protein has a $V_{max}$ for the conversion of 2-phosphoenolglycerate to phosphoenolpyruvate of about 270 μmol per minute-mg protein (based on a Δ extinction coefficient for the conversion of substrate to product of 380 $M^{-1}cm^{-1}$, see FIGS. 7 and 8) with an apparent $K_m$ for 2-phosphoenolglycerate of approximately 1.5 mM (in 0.1 M Hepes pH 7.0 containing 10 mM $MgSO_4$, 3.2 mM EDTA and 7.7 mM KCl at 30° C.) The enolase activity of the plasmin binding protein of the present invention is retained when the protein is firmly bound to the surface of the outer membrane of the streptococcal bacteria.

The plasmin binding protein of the present invention binds to plasmin and thereby hinders the inhibitory effect of $α_2$-antiplasmin. In one embodiment of the present invention, the plasmin binding protein when bound to plasmin fully prevents $α_2$-antiplasmin from inhibiting plasmin.

An embodiment of the plasmin binding protein of the present invention can also bind plasminogen. In preferred embodiments of this type, plasminogen bound to the plasmin binding protein is more readily converted to its catalytically active form by streptokinase than it is in its unbound form.

Purification of Streptococcal Surface Plasmin Binding Proteins and Homologues Thereof:

The plasmin binding protein of the present invention and homologues thereof can be purified by any number of procedures that encompass a wide variety of known purification steps. Those with skill in the art would know to refer to references, such as the Methods of Enzymology series, for greater detail and breadth. Initial steps for purifying the proteins of the present invention include salting in or salting out, such as in ammonium sulfate fractionations; solvent exclusion fractionations, e.g., an ethanol precipitation; detergent extractions to free membrane bound proteins using such detergents as Triton X-100, Tween-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl] aminoethyl (QAE) Sephadex or cellulose; or with a cation exchanger such as carboxymethyl (CM) or sulfopropyl (SP) Sephadex or cellulose. Alternative means of solid phase binding includes the exploitation of hydrophobic interactions e.g., the using of a solid support such as phenylSepharose and a high salt buffer; affinity-binding, using, e.g., plasmin bound to an activated support; immuno-binding, using e.g., an antibody to the plasmin binding protein bound to an activated support; as well as other solid phase supports including those that contain specific dyes or lectins etc. A further solid phase support technique that is often used at the end of the purification procedure relies on size exclusion, such as Sephadex and Sepharose gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Materials to perform all of these techniques are available from a variety of sources such as Sigma Chemical Company in St. Louis, Mo.

In a specific embodiment, exemplified infra, a suitable procedure for purifying a plasmin binding protein of the present invention is described as follows. One skilled in the art of protein purification would know that any such general procedure would probably need to be modified for any given protein and as such, performing the requisite modifications would not be considered undue experimentation.

Concentrated cell wall extracts, that had been dialyzed, are sequentially precipitated with ammonium sulfate (in one particular embodiment of this procedure, three ammonium sulfate fractionations were made: at 40, 60 and 80% saturation). The precipitated proteins are then dialyzed against a suitable buffer, (such as 0.05 M Tris/HCl pH 8.0, 0.1 M pyrophosphate pH 8.3, or 25 mM Hepes pH 7.4 etc.) and concentrated to an appropriate volume. The proteins in the dialyzed preparations are resolved onto a membrane (such as PVDF) and probed with labeled plasmin (or labeled plasminogen or homologue thereof). Each ammonium sulfate fraction is assayed to determine which ammonium sulfate fraction contains the plasmin binding protein. Further purification of the plasmin binding protein is performed on the ammonium sulfate fraction that contains the highest activity. The dialyzed and concentrated precipitate is placed into individual aliquots and stored at −70° C. until further use.

In one particular embodiment a strong plasmin-binding activity was found mainly associated with a 45 kDa protein. Furthermore, the plasmin binding protein activity was observed only in the preparation that precipitated between 40 to 60% ammonium sulfate saturation.

The aliquot of the dialyzed precipitate is next applied to an anion exchange column. In one particular embodiment, a Mono Q FPLC column (HR10/10, Pharmacia/LKB) equilibrated with 0.05 M Tris/HCl, pH 8.0 buffer was used. After washing the column with approximately 2–10 column volumes of the starting buffer, bound proteins are eluted with a linear salt gradient. In one embodiment the initial salt gradient is followed by a second linear salt gradient. The salt may be either monovalent or divalent. When two gradients are used, the first gradient is generally 2–5 times greater in volume than the second gradient, and covers a 2–5 fold greater range of salt concentration. In one particular embodiment, the first gradient was 70 mls and ranged from 0–0.7 M NaCl; the second gradient was 20 mls and ranged from 0.7–1.0 M NaCl.

These fractions can be assayed in any number of ways including testing for enolase activity or plasmin binding activity. In one particular embodiment, the protein elution profiles of each fraction was determined by SDS-PAGE and Coomassie blue staining. A duplicate gel was Western blotted and probed with $^{125}$I-plasmin or plasminogen as described supra. The plasmin binding protein was eluted at a 0.63 M NaCl.

Fractions showing plasmin binding activity are pooled and dialyzed against the starting buffer and re-chromatographed on an anion exchange column, e.g. a Mono Q column as described above. The fractions are again assayed and those containing the plasmin binding protein are pooled, and then concentrated. One means to obtain a final volume of less than one ml, when desired, is to use a size exclusion chromatographic technique such as a Centriprep 30 and/or a Centricon 30 concentrator (Amicon).

The concentrated sample is then applied to a size exclusion column e.g. a Superose-12 FPLC column (Pharmacia/LKB) pre-equilibrated with a suitable buffer, e.g., 0.05 M Tris/HCl, pH 8.0, fractions are assayed and those containing the plasmin binding protein are pooled. In one particular embodiment two assays were performed and only fractions that were positive for both were pooled. In this case, the plasmin binding activity and the anticipated molecular weight, 45 kDa as determined by SDS-PAGE were determined for each fraction.

The pooled fractions are then concentrated again, and mixed with high salt and applied to a hydrophobic column that has been pre-equilibrated with a suitable buffer containing a high salt concentration. In a particular embodiment, a volume ratio of 1 part concentrated sample to 3 parts 4 M ammonium sulfate was mixed prior to applying the sample to a Poros BU/M hydrophobic column pre-equilibrated with 0.05 M Tris/HCl, pH 8.0 containing 3 M ammonium sulfate.

The protein is eluted by a decreasing linear gradient of the salt. In one particular embodiment, the gradient ranged from 3.0 to 0.0. M ammonium sulfate in a 20-ml volume. In this embodiment the plasmin binding protein was eluted in one fraction at 1.32 M ammonium sulfate.

The eluted protein, now purified, is dialyzed and then stored at a concentration of between about 50 µg–10 mg/ml at −70° C. until further use.

Other sources of plasmin binding protein. Alternatives to purifying the plasmin binding protein from streptococcal cultures include genetically engineering expression of the protein from vectors introduced into host cells, or preparing the protein synthetically, e.g., using solid phase peptide synthesis techniques. This latter methodology allows for introduction of unnaturally occurring amino acid residues and peptide bond mimetics, which can enhance plasmin bonding activity, in vivo half life, or both (see below).

Synthetic Polypeptides and Fragments Thereof

The term "polypeptide" is used in its broadest sense to refer to a compound of two or more subunit amino acids, amino acid analogs, or peptidomimetics. The subunits may be linked by peptide bonds. In another embodiment, the subunit may be linked by other the bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The plasmin binding protein and active fragments thereof of the present invention may be chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile $N^\alpha$-amino protected 9-fluorenylmethoxycarbonyl (Fmoc) amino acids first described by Carpino and Han (1972, J. Org. Chem. 37:3403–3409). Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189–199; Hruby et al., 1990, Biochem J. 268:249–262); the present invention provides a method to produce a constrained peptide that incorporates random sequences at all other positions.

Constrained and cyclic peptides. A constrained, cyclic or rigidized peptide may be prepared synthetically, provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson (1980, Biophys. Biochem. Res. Commun. 94:1128–1132). A peptide in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The present invention provides strategies to systematically prepare cross-links. For example, if four cysteine residues are incorporated in the peptide sequence, different protecting groups may be used (Hiskey, 1981, in The Peptides: Analysis, Synthesis, Biology, Vol. 3, Gross and Meienhofer, eds., Academic Press: New York, pp. 137–167; Ponsanti et al., 1990, Tetrahedron 46:8255–8266). The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical amino acids that induce conformational constraints. The following non-classical amino acids may be incorporated in the peptide in order to introduce particular conformational motifs: 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); α-helix inducing analogs (Kemp et al., 1988, Tetrahedron Lett. 29:4935–4938); γ-turn inducing analogs (Kemp et al., 1989, J. Org. Chem. 54:109:115); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110:5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436. Conformationally restricted mimetics of beta turns and beta bulges, and peptides containing them, are desribed in U.S. Pat. No. 5,440,013, issued Aug. 8, 1995 to Kahn.

Derivatized and modified peptides. The present invention further provides for modification or derivatization of a peptide of the invention. Modifications of peptides are well known to one of ordinary skill, and include phosphorylation, carboxymethylation, and acylation. Modifications may be effected by chemical or enzymatic means.

In another aspect, glycosylated or fatty acylated peptide derivatives may be prepared.

Preparation of glycosylated or fatty acylated peptides is well known in the art as exemplified by the following references:

1. Garg and Jeanloz, 1985, in Advances in Carbohydrate Chemistry and Biochemistry, Vol. 43, Academic Press.
2. Kunz, 1987, in Ang. Chem. Int. Ed. English 26:294–308.
3. Horvat et al., 1988, Int. J. Pept. Protein Res. 31:499–507.
4. Bardaji et al., 1990, Ang. Chem. Int. Ed. English, 23:231.
5. Toth et al., 1990, in Peptides: Chemistry, Structure and Biology, Rivier and Marshal, eds., ESCOM Pubi., Leiden, pp. 1078–1079.
6. Torres et al., 1989, Experientia 45:574–576.
7. Torres et al., 1989, EMBO J. 8:2925–2932.
8. Hordever and Musiol, 1990, in Peptides: Chemistry, Structure and Biology, loc. cit., pp. 811–812.
9. Zee-Cheng and Olson, 1989, Biochem. Biophys. Res. Commun. 94:1128–1132.
10. Marki et al., 1977, Helv. Chem. Acta., 60:807.
11. Fuju et al. 1987, J. Chem. Soc. Chem. Commun., pp. 163–164.
12. Ponsati et al., 1990, Peptides 1990, Giralt and Andreu, eds., ESCOM Publ., pp. 238–240.
13. Fuji et al., 1987, 1988, Peptides: Chemistry and Biology, Marshall, ed., ESCOM Publ., Leiden, pp. 217–219.

There are two major classes of peptide-carbohydrate linkages. First, ether bonds join the serine or threonine hydroxyl to a hydroxyl of the sugar. Second, amide bonds join qlutamate or asparatate carboxyl groups to an amino group on the sugar. In particular, references 1 and 2, supra, teach methods of preparing peptide-carbohydrate ethers and amides. Acetal and ketal bonds may also bind carbohydrate to peptide.

Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure—$(CH_2)_nCH_3$ may be incorporated in the peptide. This and other peptide-fatty acid conjugates suitable for use in the present invention are disclosed in U.K. Patent GB-8809162.4, International Patent Application PCT/AU89/00166, and reference 5, supra.

Genes Encoding Plasmin Binding Proteins

The present invention contemplates isolation of a gene encoding a plasmin binding protein of the invention, including a full length, or naturally occurring form of the plasmin binding protein, and any antigenic fragments thereof from any bacterial strain and more particularly from streptococcus. As used herein, the term "gene" refers to an assembly of nucleotides that encode a polypeptide, and includes cDNA and genomic DNA nucleic acids.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences and synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "homologous" in all its grammatical forms refers to the relationship between proteins that possess a "common evolutionary origin," including proteins from superfamilies (e.g., the immunoglobulin superfamily) and homologous proteins from different species or bacterial strains (e.g., myosin light chain, etc.) (Reeck et al., 1987, Cell 50:667). Such proteins have sequence homology as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding plasmin binding protein, whether genomic DNA or cDNA, can be isolated from any bacterial strain, particularly from a group A streptococcus. Methods for obtaining the plasmin binding protein gene are well known in the art, as described above (see, e.g., Sambrook et al., 1989, supra).

Accordingly, any bacterial cell, preferably streptococcal bacteria, potentially can serve as the nucleic acid source for the molecular cloning of a plasmin binding protein gene. The DNA may be obtained by standard procedures known in the art from cloned DNA (e.g., a DNA "library"), by chemical synthesis, by cDNA cloning, or by the cloning of genomic DNA, or fragments thereof, purified from the desired bacterial cell (See, for example, Sambrook et al., 1989, supra; Glover, D. M. (ed.), 1985, DNA Cloning: A Practical Approach, MRL Press, Ltd., Oxford, U.K. Vol. I, II). Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired plasmin binding protein gene may be accomplished in a number of ways. For example, if an amount of a portion of a plasmin binding protein gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). For example, a set of oligonucleotides corresponding to the partial amino acid sequence information obtained for the plasmin binding protein can be prepared and used as probes for DNA encoding plasmin binding protein, as was done in a specific example, infra, or as primers for cDNA or mRNA (e.g., in combination with a poly-T primer for RT-PCR). Preferably, a fragment is selected that is highly unique to the plasmin binding protein of the present invention. Those DNA fragments with substantial homology to the probe will hybridize. As noted above, the greater the degree of homology, the more stringent hybridization conditions can be used. In a specific embodiment, stringency hybridization conditions are used to identify a homologous plasmin binding protein gene.

Further selection can be carried out on the basis of the properties of the gene, e.g., if the gene encodes a protein product having the isoelectric, electrophoretic, amino acid composition, or partial amino acid sequence of plasmin binding protein as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for plasmin binding protein. For example, the rabbit polyclonal antibody to plasmin binding protein, described in detail infra, can be used to confirm expression of plasmin binding protein. In another aspect, a protein that has an apparent molecular weight of 45 kDa and has enolase activity is a good candidate for plasmin binding protein.

A plasmin binding protein gene of the present invention can also be identified by mRNA selection, i.e., by nucleic acid hybridization followed by in vitro translation. In this procedure, nucleotide fragments are used to isolate complementary mRNAs by hybridization. Such DNA fragments may represent available, purified plasmin binding protein DNA, or may be synthetic oligonucleotides designed from the partial amino acid sequence information. Immunoprecipitation analysis or functional assays (e.g., tyrosine phosphatase activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against plasmin binding protein, such as the rabbit polyclonal anti-streptococcal plasmin binding protein antibody described herein.

A radiolabeled plasmin binding protein cDNA can be synthesized using the selected mRNA (from the adsorbed polysomes) as a template. The radiolabeled mRNA or cDNA may then be used as a probe to identify homologous plasmin binding protein DNA fragments from among other genomic DNA fragments.

The present invention also relates to cloning vectors containing genes encoding analogs and derivatives of the plasmin binding protein of the invention, that have the same or homologous functional activity as plasmin binding protein, and homologs thereof from other bacterial strains. The production and use of derivatives and analogs related to the plasmin binding protein are within the scope of the present invention.

Plasmin binding protein derivatives and analogs as described above can be made by altering encoding nucleic acid sequences by substitutions, additions or deletions that provide for functionally equivalent molecules. Preferably, derivatives are made that have enhanced or increased functional activity relative to native plasmin binding protein. Alternatively, such derivatives may encode soluble fragments of plasmin binding protein extracellular domain that have the same or greater affinity for plasmin. Such soluble derivatives may be potent inhibitors of plasmin binding to $\alpha_2$-antiplasmin.

Due to the degeneracy of nucleotide coding sequences, other DNA sequences which encode substantially the same amino acid sequence as a plasmin binding protein gene may be used in the practice of the present invention. These include but are not limited to allelic genes, homologous genes from other species, and nucleotide sequences comprising all or portions of plasmin binding protein genes which are altered by the substitution of different codons that encode the same amino acid residue within the sequence, thus producing a silent change. Likewise, the plasmin binding protein derivatives of the invention include, but are not limited to, those containing, as a primary amino acid sequence, all or part of the amino acid sequence of a plasmin binding protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding plasmin binding protein derivatives and analogs of the invention can be produced by various methods known in the art. The manipulations which result in their production can occur at the gene or protein level. For example, the cloned plasmin binding protein gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of plasmin binding protein, care should be taken to ensure that the modified gene remains within the same translational reading frame as the plasmin binding protein gene, uninterrupted by translational stop signals, in the gene region where the desired activity is encoded.

Additionally, the plasmin binding protein-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated plasmin binding protein gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification,* H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli,* bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., E. coli, and facile purification for subsequent insertion into an appropriate expression cell line, if such is desired. For example, a shuttle vector, which is a vector that can replicate in more than one type of organism, can be prepared for replication in both E. coli and Saccharomyces cerevisiae by linking sequences from an E. coli plasmid with sequences form the yeast 2μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of Plasmin Binding Proteins

The nucleotide sequence coding for the plasmin binding protein, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding plasmin binding protein of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector. As pointed out above, potential chimeric partners for the plasmin binding protein include plasmin, plasminogen activators and fibrin binding domains. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant plasmin binding protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding plasmin binding protein is cultured in an appropriate cell culture medium under conditions that provide for expression of plasmin binding protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of plasmin binding protein may be controlled by any promoter/enhancer element known in the art, but these regulatory elements must be functional in the host selected for expression. Promoters which may be used to control plasmin binding protein gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing a nucleic acid encoding a plasmin binding protein of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding plasmin binding protein is inserted within the "selection marker" gene sequence of the vector, recombinants containing the plasmin binding protein insert can be identified by the absence of the plasmin binding protein gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systerns, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedron initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEB-VHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Yeast expression systems can also be used according to the invention to express OB polypeptide. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the present invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Antibodies to the Plasmin Binding Protein

According to the present invention, the plasmin binding protein as purified from natural sources such as streptococci bacteria, or produced recombinantly or by chemical synthesis, and fragments or other derivatives or analogs thereof, including fusion proteins, may be used as an immunogen to generate antibodies that recognize the plasmin binding protein. Such antibodies include but are not limited to polyclonal, monoclonal, chimeric, single chain, Fab fragments, and a Fab expression library. The anti-plasmin binding protein antibodies of the invention may be cross reactive, e.g., they may recognize the plasmin binding protein from different bacterial strains. Polyclonal antibodies have greater likelihood of cross reactivity. Alternatively, an antibody of the invention may be specific for a single form of the plasmin binding, such as the streptococci plasmin binding protein, SEN.

Various procedures known in the art may be used for the production of polyclonal antibodies to the plasmin binding protein or derivative or analog thereof. For the production of antibody, various host animals can be immunized by injection with the plasmin binding protein, or a derivative (e.g., fragment or fusion protein) thereof, including but not limited to rabbits, mice, rats, sheep, goats, etc. In one embodiment, the plasmin binding protein or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the plasmin binding protein, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy,* Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for an plasmin binding protein together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce plasmin binding protein-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for a plasmin binding protein, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of the plasmin binding protein, one may assay generated hybridomas for a product which binds to the plasmin binding protein fragment containing such epitope. For selection of an antibody specific to the plasmin binding protein from a particular strain of bacteria, one can select on the basis of positive binding with plasmin binding protein expressed by or isolated from bacteria of that specific strain.

The foregoing antibodies can be used in methods known in the art relating to the localization and activity of the plasmin binding protein, e.g., for Western blotting, imaging plasmin binding protein in situ, measuring levels thereof in appropriate physiological samples, etc. using any of the detection techniques mentioned above or known in the art.

In a specific embodiment, antibodies that agonize or antagonize the activity of plasmin binding protein can be generated. Such antibodies can be tested using the assays described infra for identifying ligands.

Crosslinking Agents

The plasmin binding protein may be conjugated to another molecule, such as an anti-fibrin antibody, through a polyfunctional molecule, i.e., a polyfunctional crosslinker. As used herein, the term "polyfunctional molecule" encompasses molecules having one functional group that can react more than one time in succession, such as formaldehyde (although formaldehyde is not indicated for use due to its potential carcinogenicity), as well as molecules with more than one reactive group. As used herein, the term "reactive group" refers to a functional group on the crosslinker that reacts with a functional group on a molecule (e.g., peptide, protein, or carbohydrate) so as to form a covalent bond between the cross-linker and that molecule. The term "functional group" retains its standard meaning in organic chemistry. The polyfunctional molecules which can be used are preferably biocompatible linkers, i.e., they are noncarcinogenic, nontoxic, and substantially non-immunogenic in vivo. Polyfunctional cross-linkers such as those known in the art and described herein can be readily tested in animal models to determine their biocompatibility. The polyfunctional molecule is preferably bifunctional. As used herein, the term "bifunctional molecule" refers to a molecule with two reactive groups. The bifunctional molecule may be heterobifunctional or homobifunctional. A heterobifunctional cross-linker allows for vectorial conjugation. It is particularly preferred for the polyfunctional molecule to be sufficiently soluble in water for the cross-linking reactions to occur in aqueous solutions such as in aqueous solutions buffered at pH 6 to 8, and for the resulting conjugate to remain water soluble for more effective biodistribution.

Typically, the polyfunctional molecule covalently bonds with an amino or a sulfhydryl functional group. However, polyfunctional molecules reactive with other functional groups, such as carboxylic acids or hydroxyl groups, are contemplated in the present invention.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaradehyde and subaraldehyde. The use of glutaraldehyde as a cross-linking agent was disclosed by Poznansky et al., Science 223, 1304–1306 (1984). Homobifunctional molecules having at least two active ester units include esters of dicarboxylic acids and N-hydroxysuccinimide. Some examples of such N-succinirnidyl esters include disuccinimidyl suberate and dithio-bis-(succinimidyl propionate), and their soluble bis-sulfonic acid and bis-sulfonate salts such as their sodium and potassium salts. These homobifunctional reagents are available from Pierce Chemical Co., Rockford, Ill.

The heterobifunctional molecules have at least two different reactive groups. The reactive groups react with different functional groups, e.g., present on the agent and the inhibitor. These two different functional groups that react with the reactive group on the heterobifunctional cross-linker are usually an amino group, e.g., the epsilon amino group of lysine; a sulfhydryl group, e.g., the thiol group of cysteine; a carboxylic acid, e.g., the carboxylate on aspartic acid; or a hydroxyl group, e.g., the hydroxyl group on serine. Analogous functional groups can be found on carbohydrates, peptides, and proteins.

When a reactive group of a heterobifunctional molecule forms a covalent bond with an amino group, the covalent bond will usually be an amido or imido bond. The reactive group that forms a covalent bond with an amino group may, for example, be an activated carboxylate group, a halocarbonyl group, or an ester group. The preferred halocarbonyl group is a chlorocarbonyl group. The ester groups are preferably reactive ester groups such as, for example, an N-hydroxy-succinimide ester group or that of Mal-Sac-HNSA.

The other functional group typically is either a thiol group, a group capable of being converted into a thiol group, or a group that forms a covalent bond with a thiol group.

The covalent bond will usually be a thioether bond or a disulfide. The reactive group that forms a covalent bond with a thiol group may, for example, be a double bond that reacts with thiol groups or an activated disulfide. A reactive group containing a double bond capable of reacting with a thiol group is the maleimido group, although others, such as acrylonitrile, are also possible. A reactive disulfide group may, for example, be a 2-pyridyldithio group or a 5,5'-dithio-bis-(2-nitrobenzoic acid) group. Some examples of hetero-bifunctional reagents containing reactive disulfide bonds include N-succinimidyl 3-(2-pyridyl-dithio)propionate (Carlsson, et al., 1978, Biochem J., 173:723–737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate.

Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxy-succinimide ester. The sodium sulfonate salt of succinimidyl m-maleimidobenzoate is preferred. Many of the above-mentioned heterobifunctional reagents and their sulfonate salts are available from Pierce Chemical Co., Rockland, Ill.

Labels

Suitable labels include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. b 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enymology,* 70. 419–439, 1980 and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as $[^{35}S]$-methionine or $[^{32}P]$-orthophosphate. In addition to metabolic (or biosynthetic) labeling with $[^{35}S]$-methionine, the invention further contemplates labeling with $[^{14}C]$-amino acids and $[^{3}H]$-amino acids (with the tritium substituted at non-labile positions).

Solid Phase Supports

A solid phase support for use in the present invention will be inert to the reaction conditions for binding. A solid phase support for use in the present invention must have reactive groups in order to attach a binding partner, such as the plasmin binding protein or an antibody to the plasmin binding protein, or for attaching a linker or handle which can serve as the initial binding point for any of the foregoing. In another embodiment, the solid phase support may be a useful chromatographic support, such as the carbohydrate polymers SEPHAROSE, SEPHADEX, agarose. As used herein, a solid phase support is not limited to a specific type of support. Rather a large number of supports are available and are known to one of ordinary skill in the art. Solid phase supports include silica gels, resins, derivatized plastic films, glass beads, cotton, plastic beads, alumina gels, magnetic beads, membranes (including but not limited to nitrocellulose, cellulose, nylon, and glass wool), plastic and glass dishes or wells, etc. For example, solid phase supports used for peptide or oligonucleotide synthesis can be used, such as polystyrene resin (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, Calif.). In synthesis of oligonucleotides, a silica based solid phase support may be preferred. Silica based solid phase supports are commercially available (e.g., from Peninsula Laboratories, Inc.; and Applied Biosystems, Inc.).

Derivatives of the Plasmin Binding Protein

The plasmin binding protein of the present invention may be derivatized by the attachment of one or more chemical moieties to the protein moiety. The chemically modified derivatives may be further formulated for intraarterial, intraperitoneal, intramuscular subcutaneous, intravenous, oral, nasal, pulmonary, topical or other routes of administration. Chemical modification of biologically active component or components may provide additional advantages under certain circumstances, such as increasing the stability and circulation time of the component or components and decreasing immunogenicity. See U.S. Pat. No. 4,179,337, Davis et al., issued Dec. 18, 1979. For a review, see Abuchowski et al., in *Enzymes as Drugs* (J. S. Holcerberg and J. Roberts, eds. pp. 367–383 (1981)). A review article describing protein modification and fusion proteins is Francis, 1992, *Focus on Growth Factors* 3:4–10, Mediscript: Mountview Court, Friern Barnet Lane, London N20, OLD, UK.

Chemical Moieties For Derivatization. The chemical moieties suitable for derivatization may be selected from among water soluble polymers. The polymer selected should be water soluble so that the component to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co- polymers, polyoxyethylated polyols and polyvinyl alcohol. Polyethylene glycol propionaldenhyde may have advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to component or components molecules will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the component or components with consideration of effects on functional or antigenic domains of the protein. There are a number of attachment methods available to those skilled in the art, e.g., EP 0 401 384 herein incorporated by reference (coupling PEG to G-CSF), see also Malik et al., 1992, Exp. Hematol. 20:1028–1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the N- terminal amino acid residues; those having a free carboxyl group include aspartic acid residues glutamic acid residues and the C-terminal amino acid residue. Sulfhydryl groups may also be used as a reactive group for attaching the polyethylene glycol molecule(s). Preferred for therapeutic purposes is attachment at an amino group, such as attachment at the N-terminus or lysine group.

One may specifically desire N-terminally chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemically modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at pH which allows one to take advantage of the $PK_a$ differences between the e-amino groups of the lysine residues and that of the a-amino group of the N-terminal residue of the protein. By such selective derivatization attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol proprionaldehyde, containing a single reactive aldehyde, may be used.

Vaccination and Passive Immune Therapy

Active immunity against Gram positive bacteria can be induced by immunization (vaccination) with an immunogenic amount of a plasma binding protein of the present invention, or an antigenic derivative or fragment thereof, and an adjuvant, wherein the plasma binding protein, or antigenic derivative or fragment thereof, is the antigenic component of the vaccine. Preferably, the protein is conjugated to the carbohydrate capsule or capsules of one or more species of Gram positive bacterium. Covalent conjugation of a protein to a carbohydrate is well known in the art. Generally, the conjugation can proceed via a carbodiimide condensation reaction.

The plasma binding protein of the present invention alone or conjugated to a capsule or capsules cannot cause bacterial infection, and the active immunity elicited by vaccination with the protein according to the present invention can result in both an immediate immune response and an immunological memory, and thus provide long-term protection against infection by the bacterium. The plasma binding proteins of the present invention, or antigenic fragments thereof, can be prepared in an admixture with an adjuvant to prepare a vaccine. Preferably, the plasma binding protein, or derivative or fragment thereof, used as the antigenic component of the vaccine is an adhesin. More preferably, the plasma binding protein, or derivative or fragment thereof, used as the antigenic component of the vaccine is an antigen common to all or many strains of a species of Gram positive bacteria, or common to closely related species of bacteria. Most preferably, the antigenic component of the vaccine is an adhesin that is a common antigen.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

An alternative to a traditional vaccine comprising an antigen and an adjuvant involves the direct in vivo introduction of DNA encoding the antigen into tissues of a subject for expression of the antigen by the cells of the subject's tissue. Such vaccines are termed herein "nucleic acid-based vaccines." Since the plasmin binding protein gene by definition contains a signal sequence, expression of the gene in cells of the tissue results in secretion of membrane association of the expressed protein. Alternatively, the expression vector can be engineered to contain an autologous signal sequence instead of the plasmin binding protein signal sequence. For example, a naked DNA vector (see, e.g., Ulmer et al., 1993, Science 259:1745–1749), a DNA vector transporter (e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990), or a viral vector containing the desired plasmin binding protein gene can be injected into tissue. Suitable viral vectors include retroviruses that are packaged in cells with amphotropic host range (see Miller, 1990, Human Gene Ther. 1:5–14; Ausubel et al., *Current Protocols in Molecular Biology, § 9*), and attenuated or defective DNA virus, such as but not limited to herpes simplex virus (HSV) (see, e.g., Kaplitt et al., 1991, Molec. Cell. Neurosci. 2:320–330), papillomavirus, Epstein Barr virus (EBV), adenovirus (see, e.g., Stratford-Perricaudet et al., 1992, J. Clin. Invest. 90:626–630), adeno-associated virus (AAV) (see, e.g., Samulski et al., 1987, J. Virol. 61:3096–3101; Samulski et al., 1989, J. Virol. 63:3822–3828), and the like. Defective viruses, which entirely or almost entirely lack viral genes, are preferred. Defective virus is not infective after introduction into a cell. Vectors containing the nucleic acid-based vaccine of the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Either vaccine of the invention, i.e., a vaccines comprising a plasmin binding protein antigen or antigenic derivative or fragment thereof, or a plasmin binding protein nucleic acid vaccine, can be administered via any parenteral route, including but not limited to intramuscular, intraperitoneal, intravenous, and the like. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen.

Since immune cells are continually replicating, they are ideal target for retroviral vector-based nucleic acid vaccines, since retroviruses require replicating cells.

Passive immunity can be conferred to an animal subject suspected of suffering an infection with a Gram negative bacterium by administering antiserum, polyclonal antibodies, or a neutralizing monoclonal antibody against the Gram positive bacterium to the patient. Although passive immunity does not confer long term protection, it can be a valuable tool for the treatment of a bacterial infection of a subject who has not been vaccinated. Passive immunity is particularly important for the treatment of antibiotic resistant strains of Gram positive bacteria, since no other therapy is available. Preferably, the antibodies administered for passive immune therapy are autologous antibodies. For example, if the subject is a human, preferably the antibodies are of human origin or have been "humanized," in order to minimize the possibility of an immune response against the antibodies.

An analogous therapy to passive immunization is administration of an amount of a plasmin binding protein sufficient to inhibit adhesion of the bacterium to its target cell. The required amount can be determined by one of ordinary skill using standard techniques.

The active or passive vaccines of the invention, or the administration of the plasmin binding protein, can be used to protect an animal subject from infection of a Gram positive bacteria. Thus, a vaccine of the invention can be used in birds, such as chickens, turkeys, and pets; in mammals, preferably a human, although the vaccines of the invention are contemplated for use in other mammalian species, including but not limited to domesticated animals (canine and feline); farm animals (bovine, ovine, equine, caprine, porcine, and the like); rodents; and undomesticated animals.

Gene Therapy and Transgenic Vectors

In one embodiment, a gene encoding a plasmin binding protein of the present invention or polypeptide domain fragment thereof is introduced in vivo in a viral vector for thrombolytic or vaccine uses. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, adipose tissue can be specifically targeted. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828 (1989)].

Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988)]. The use of cationic lipids may promote encapsulation of negatively charged nucleic acids, and also promote fusion with negatively charged cell membranes [Felgner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

In a preferred embodiment of the present invention, a gene therapy vector as described above employs a transcription control sequence operably associated with the sequence for the plasmin binding protein inserted in the vector. This specific expression vector of the present invention can be used in gene therapy. Such an expression vector is particularly useful to regulate expression of a therapeutic plasmin binding protein gene. In one embodiment, the present invention contemplates constitutive expression of the plasmin binding protein gene, even if at low levels. In a further embodiment, the present invention provides for co-expression of plasmin binding protein of the present invention and a therapeutic plasminogen activator by providing a gene therapy expression vector comprising DNA sequences for both proteins. In a related embodiment, these elements are provided on two separate vectors.

Administration of Therapeutic Compositions

According to the invention, the component or components of a therapeutic composition of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. More preferably, where administration of the plasmin binding protein is to dissolve a particular blood clot, it may be introduced by injection into the clot or into tissues surrounding the clot.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Nasal delivery: Nasal delivery of a pharmaceutical composition of the present invention is particularly contemplated. Nasal delivery with or without the aid of a mucosal penetration enhancer, allows the passage of a p harmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize a n a erosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the pharmaceutical composition.

The term "mucosal penetration enhancer" refers to a reagent that increases the rate or facility of transmucosal penetration of the e.g., the plasmin binding protein, such as but not limited to, an aprotic solvent, a bile salt, fatty acid, surfactant or alcohol. In specific embodiments, the permeation enhancer can be sodium cholate, sodium dodecyl sulphate, so dium deoxycholate, taurodeoxycholate, sodium glycocholate, dimethylsulfoxide or ethanol. Suitable penetration enhancers also include glycyrrhetinic acid (U.S. Pat. No. 5,112,804 to Kowarski) and polysorbate-80, the latter preferably in combination with an non-ionic surfactant such as nonoxynol-9, laureth-9, poloxamer-124, octoxynol-9, or lauramide-DEA (European Patent EP 0 242 643 B1 by Stoltz).

Pulmonary Delivery. Also contemplated herein is pulmonary delivery of the pharmaceutical compositions of the present invention. A pharmaceutical composition of the present invention is delivered to the lungs of a mammal while inhaling and traverses across the lung epithelial lining to the blood stream. Other reports of this include Adjei et al. [*Pharmaceutical Research,* 7:565–569 (1990); Adjei et al., *International Journal of Pharmaceutics,* 63:135–144 (1990) (leuprolide acetate); Braquet et al., *Journal of Cardiovascular Pharmacology,* 13(suppl. 5):143–146 (1989) (endothelin-1); Hubbard et al., *Annals of Internal Medicine,* Vol. III, pp. 206–212 (1989) ($\alpha$1-antitrypsin); Smith et al., *J. Clin. Invest.* 84:1145–1146 (1989) ($\alpha$-1-proteinase); Oswein et al., "Aerosolization of Proteins", *Proceedings of Symposium on Respiratory Drug Delivery II,* Keystone, Colo., March, (1990) (recombinant human growth hormone); Debs et al., *J. Immunol.* 140:3482–3488 (1988) (interferon-$\gamma$ and tumor necrosis factor alpha); Platz et al., U.S. Pat. No. 5,284,656 (granulocyte colony stimulating factor)]. A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the polypeptides of the present invention alone or together with one or more other proteins or reagents. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified plasmin binding protein of the present invention may also be prepared in different formulations depending on the type of chemical modification or the type of device employed.

Formulations suitable for use with a nebulizer, either jet or ultrasonic, will typically comprise the polypeptides of the present invention (or derivative) dissolved in water at a concentration of about 0.1 to 25 mg of biologically active ingredients of the plasmin binding protein per mL of solution. The formulation may also include a buffer and a simple sugar (e.g., for stabilization and regulation of osmotic pressure of a pharmaceutical composition of the present invention). The nebulizer formulation may also contain a surfactant, to reduce or prevent surface induced aggregation of the polypeptides of the present invention caused by atomization of the solution in forming the aerosol.

Formulations for use with a metered-dose inhaler device will generally comprise a finely divided powder containing a pharmaceutical composition of the present invention suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

The liquid aerosol formulations contain a plasmin binding protein of the present invention alone or together with one or more other reagents or proteins, and a dispersing agent in a physiologically acceptable diluent. The dry powder aerosol formulations of the present invention consist of a finely divided solid form of a pharmaceutical composition of the present invention and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of nasal or pulmonary administration of a drug are well known in the art, and manipulation of formulations, aerosolization means and construction of a delivery device require at most routine experimentation by one of ordinary skill in the art.

In a particular embodiment, the mass median dynamic diameter will be 5 micrometers or less in order to ensure that the drug particles reach the lung alveoli (Wearley, L. L., 1991, 1991, Crit. Rev. in Ther. Drug Carrier Systems 8:333).

As noted above, the device for aerosolization can be a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

Often, the aerosolization of a liquid or a dry powder formulation for inhalation into the lung will require a propellent. The propellent may be any propellant generally used in the art. Specific nonliniting examples of such useful propellants are a chlorofluorocarbon, a hydrofluorocarbon, a hydrochlorofluorocarbon, or a hydrocarbon, including trifluoromethane, dichlorodifluoromethane, dichlorotetrafluoroethanol, and 1,1,1,2-tetrafluoroethane, or combinations thereof.

Systems of aerosol delivery, such as the pressurized metered dose inhaler and the dry powder inhaler are disclosed in Newman, S. P., *Aerosols and the Lung,* Clarke, S. W. and Davia, D. editors, pp. 197–22 and can be used in connection with the present invention.

In a further embodiment, as discussed in detail infra, an aerosol formulation of the present invention can include other therapeutically or pharmacologically active ingredients in addition to plasmin binding protein of the present invention such as but not limited to a plasminogen activator or an antibody for fibrin.

In general, a plasmin binding protein of the present invention is introduced into the subject in the aerosol form in an amount between about 0.01 mg per kg body weight of the mammal up to about 1 mg per kg body weight of said mammal. In a specific embodiment, the dosage is administered as needed. One of ordinary skill in the art can readily determine a volume or weight of aerosol corresponding to this dosage based on the concentration of pharmaceutical composition of the present invention in an aerosol formulation of the invention.

Liquid Aerosol Formulations

The present invention provides aerosol formulations and dosage forms for use in treating subjects in need of thrombolytic therapy. In general such dosage forms contain a pharmaceutical composition of the present invention in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0–8.0 range, or water.

As mentioned above, the liquid aerosol formulation of the present invention may include, as optional ingredients, pharmaceutically acceptable carriers, diluents, solubilizing or emulsifying agents, surfactants and excipients.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. As indicated above, such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

The present invention further contemplates liquid aerosol formulations comprising a pharmaceutical composition of the present invention and another therapeutically effective drug, such as a benzodiazepine or a narcotic analgesic.

Aerosol Dry Powder Formulations:

It is also contemplated that the present aerosol formulation can be prepared as a dry powder formulation comprising a finely divided powder form of a pharmaceutical composition of the present invention and a dispersant.

Formulations for dispensing from a powder inhaler device will comprise a finely divided dry powder containing pharmaceutical composition of the present invention and may also include a bulking agent, such as lactose, sorbitol, sucrose, or mannitol in amounts which facilitate dispersal of the powder from the device, e.g., 50 to 90% by weight of the formulation. The pharmaceutical composition of the present invention should most advantageously be prepared in particulate form with an average particle size of less than 10 mm (or microns), most preferably 0.5 to 5 mm, for most effective delivery to the distal lung.

In another embodiment, the dry powder formulation can comprise a finely divided dry powder containing a pharmaceutical composition of the present invention, a dispersing agent and also a bulking agent. Bulking agents useful in conjunction with the present formulation include such agents as lactose, sorbitol, sucrose, or mannitol, in amounts that facilitate the dispersal of the powder from the device.

The present invention further contemplates dry powder formulations comprising a pharmaceutical composition of the present invention and another therapeutically effective drug, such as a benzodiazepine or a narcotic analgesic.

In another embodiment, the therapeutic compound can be delivered in a vesicle, in particular a liposome [see Langer, *Science* 249:1527–1533 (1990); Treat et al., in *Liposomes in the Therapy of Infectious Disease and Cancer,* Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing the plasmin binding protein when it is co-administered with plasmin or a plasminogen activator.

In yet another embodiment, the therapeutic compound can be delivered in a controlled release system. For example, a pharmaceutical composition of the present invention may be administered using intravenous infusion, an implantable osmotic pump, a transdermal patch, liposomes, or other modes of administration. In one embodiment, a pump may be used [see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release,* Langer and Wise (eds.), CRC Press: Boca Raton, Fla. (1974); *Controlled Drug Bioavailability, Drug Product Design and Performance,* Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of the therapeutic target, i.e., the heart, thus requiring only a fraction of the systemic dose [see, e.g., Goodson, in *Medical Applications of Controlled Release,* supra, vol. 2, pp. 115–138 (1984)]. Preferably, a controlled release device is introduced into a subject in proximity of the site of the deleterious clot.

Other controlled release systems are discussed in the review by Langer [*Science* 249:1527–1533 (1990)].

In a further aspect, recombinant cells that have been transformed with the plasmin binding protein gene and that express high levels of the polypeptide can be transplanted into a subject in need of a greater concentration of active plasmin. Preferably autologous cells transformed with the plasmin binding protein are transplanted to avoid rejection; alternatively, technology is available to shield non-autologous cells that produce soluble factors within a polymer matrix that prevents immune recognition and rejection.

Thus, the plasmin binding protein can be delivered by intravenous, intraarterial, intraperitoneal, intramuscular, or subcutaneous routes of administration. Alternatively, the plasmin binding protein properly formulated, can be administered oral administration. A constant supply of the plasrnin binding protein can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

A subject in whom administration of the plasmin binding protein is an effective therapeutic regiment for thrombolytic therapy is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animal such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In particular an important disease in domestic cattle involves fibrin pneumonia that occurs in cows infected with *Pasteurella haemolytica.* There has long been a need for a method to treat the surprisingly common fibrin deposits in the lungs of afflicted animals, who otherwise suffocate and die. The present invention offers a treatment for this disease, by administrating, as detailed above, a pharmaceutical composition of the present invention.

The present invention may be better understood by reference to the following non-limiting Examples, which are provided as exemplary of the invention.

EXAMPLES

Materials and Methods

Human Plasminogen and Plasmin: Purified human plasminogen and plasmin (Lysine-plasmin) were purchased commercially (Sigma Chem Co., St.Louis, Mo. USA). Plasmin was also generated from plasminogen by incubation with urokinase (20 units/ml, Sigma Chemical Co., St. Louis, Mo., U.S.A.) in 0.15M Veronal buffered saline, pH 7.4, containing 1 mM MgCl2, 0.15 mM $CaCl_2$ and 0.1% gelatin (VBS-gel buffer), that also contained 0.02M lysine. Conversion of plasminogen to plasmin was maximal after 45 min at 37° C. [Lottenberg et al., (1987), Infection and Immunity, 55; 1914–1918]. This method consistently converted more than 95% of the single chain zymogen molecule plasminogen to heavy and the light chain of the plasmin molecule.

Radioiodination of Plasminogen and Plasmin: Purified plasminogen and plasmin were iodinated ($^{125}I$)by the chloramine-T method, using Iodobeads (Pierce Chem Co. Rockford, Ill., USA) as described [Pancholi, V. and Fischetti, V. A. (1992), J Exp. Med, see Supra]. The labelled proteins were separated from free iodine by passage over a G-25 column (PD-10, Pharmacia Biotech) and collected in 0.15 M Veronal buffered saline, pH 7.4, containing 1 mM MgCl2, 0.15 mM $CaCl_2$ and 0.1% gelatin (VBS-Gel). The labeled proteins were stored at −70° C.

Generation of Plasmin and its Radioiodination: Plasmin was also generated from the $^{125}I$-radiolabeled plasminogen by incubation with urokinase (20 units/ml, Sigma) in VBS-gel that contained lysine. More than 95% of the radioactivity was found to be retained with plasmin. Thus the specific radioactivity of the labeled plasmin and plasminogen was found to be essentially the same. Furthermore, the specific radioactivity of the commercially available purified plasmin (See above) and urokinase-generated plasmin was also found to be the same. Typically, specific radioactivity of the $^{125}$I-labeled plasmin/plasminogen was achieved in a range of $1.2$–$2.0 \times 10^6$ cpm/μg protein.

Bacteria: Group A β-hemolytic streptococcal strains of various M types and standard strains used for streptococcal grouping were from The Rockefeller University Culture Collection (New York, N.Y.) and are listed as follows: M2(D626), M4(F694), M6(D471), M9(F690), M11(F743), M15(D176A), M22(D943), M25(B554), M35(C171), M40 (C270), M44(C757), M49(B910), M51(A291), M58(D632), M60(D630), M61(D336), M62(D458), M63(D459), M66 (D794), group B (0902), group C(C74), group D(D76), group E(K131), group F (F68C), group G (D166B), group H (F90A), group L (D167B), and group N (C559). These strains were grown in Todd-Hewitt broth overnight and washed once with 0.05 M ammonium bicarbonate pH 8.0 followed by two consecutive washes in 0.05 M phosphate buffer, pH 6.1 to eliminate the soluble plasminogen activator, streptokinase which could otherwise interfere in the present study. Type M6 (D471) streptococci [Pancholi, V. and Fischetti, V. A. (1992) J. Exp. Med 176:415–426] were used for the isolation of the plasmin(ogen) binding protein, SEN, while the other strains were used to study the prevalence of the SEN proteins in different streptococcal groups and serotypes.

Streptococcal cell wall extraction by lysin or mutanolysin treatment: M6 strain D471 was grown to a stationary phase of culture at 37° C. for 18 h in 4–6 liter batches of Todd-Hewitt broth. Bacteria were pelleted by centrifugation and washed (See above) and then resuspended in 0.05 M phosphate buffer (2% of the original culture volume) containing 30% raffinose, 5 mM dithiothreitol and 5 mM EDTA. Lysin [Fischetti et al., (1971) J. Exp. Med. 133, 1105–1117.] was added to the bacterial suspension (120 U/ml) and incubated at 37° C. for 90 min with constant slow stirring. The resulting protoplasts were sedimented at 15,000×g for 30 min at 4° C. The supernatant was dialyzed against 50 mM Tris-HCl pH 8.0 and concentrated 10-fold using Centriprep-30 concentrators (Amicon). The muralytic enzyme mutanolysin (20 μg/ml, Sigma chemical Co) was used to prepare cell wall extracts of each grouping strain suspended in 50 mM Tris-HCl buffer pH 6.8 containing 5 mM EDTA, 5 mM MgCl$_2$, and 30% raffinose. The cell wall extracts were separated by centrifugation after 60 min incubation of the reaction mixture at 37° C.

Binding Assay: Proteins in the bacterial extracts, chromatography fractions or protein standards were resolved on 12% SDS-PAGE gels, with a reducing agent and Western blotted onto a PVDF membrane as described [Pancholi, V. and Fischetti, V. A. (1988) J.Bacteriol.. 170:2618, (1989) J.Exp.Med. 170: 2119]. Western blots were blocked for 2–3 h in 5.0 mM sodium diethylbarbiturate, 0.15 M NaCl, 0.5% BSA acidified, 0.5% gelatin, 0.15% Tween-20, 0.04% NaN$_3$, pH 7.4. The blots were probed for 3–4 h at room temperature in the blocking buffer containing 2.0 mM PMSF and $^{125}$I-labeled human plasmin or plasminogen $3 \times 10^5$ cpm/ml. The probed blots were then washed several times with blocking buffer containing 0.01 M EDTA, 0.5 M NaCl, 0.25% gelatin, 0.15% Tween-20, 0.25% BSA, and 0.04% NaN$_3$, dried and exposed to Kodak X-OMAT AR film with an intensifying screen for 12–15 h at −70° C. (see FIG. 1).

Production and purification of rabbit polyclonal antisera against the SEN protein: Polyclonal antibodies to SEN were prepared in New Zealand white rabbits. Rabbits were immunized subcutaneously with 150 μg of purified SEN emulsified in complete Freund's adjuvant (1:1) at multiple sites. Rabbits were boosted twice each with 150 μg of the purified protein in incomplete Freund's adjuvant (1:1) at an interval of 3 weeks. Rabbits were bled 10 days after the third immunization. All sera were filter sterilized and stored at 4° C. SEN-specific antibodies were affinity purified from the polyclonal sera on a column containing ~2 mg of the purified SEN linked covalently to ultralink carboxy beads with 1-ethyl-3-(3-dimethyl aminopropyl) carbodiimide,(EDC), (Pierce Chemical Co., Rockland, Ill.). The protein and affinity matrix (0.5 g) were suspended in a final volume of 2.0 ml of 0.1 M phosphate buffer pH 6.5 and rotated at room temperature for 3–4 hours in a one cm diameter column. The protein-coupled matrix was then washed sequentially with 1.5% NaCl; 0.3 M ethanolamine, pH 7.0; 0.9% NaCl; 0.5 M propionic acid; 0.9% NaCl; and then with 0.01 phosphate buffered saline, pH 7.4. Anti-SEN antisenim (2–3 ml) was adsorbed to the immunoadsorbent column using 0.05 M Tris/HCl pH 8.0 as an initial buffer. Specific anti-SEN antibodies were then eluted with 0.2 M Glycine/HCl buffer, pH 2.5. The eluted antibodies were then dialyzed against the starting buffer and concentrated. These antibodies were further purified on a Protein A column-Sepharose CL-4B using a similar strategy of binding and elution. The resulting SEN-specific affinity purified IgG was used for further immunological analyses.

Production and purification of monoclonal antibodies against SEN: BALB/c×SJL-F1 mice were subcutaneously immunized with 30 μg of purified SEN in complete Freund's adjuvant. After 3 weeks, the mice were bled and tested for antibodies to SEN by ELISA and Western blots using a crude cell wall extract of group A M6 strain D471 bacteria. Affinity purified rabbit polyclonal antibodies against SEN were used as control antibodies in these assays. Mice with high antibody titres were given a second dose of antigen in distilled water, intraperitoneally. Mouse spleens were excised 3–3.5 days after the last booster. The spleen cell fusion to P3-NS1/1AG4-1(NS-1) myeloma cells was performed as described (Kohler, G. and Milstein, C. (1976) Eur. J.Immunol.6:511–519, Galfre, G. S., Howe, C., Milstein, C., Butcher, G. W., and Howard, J. C. (1977) Nature, 266, 550–552.) Hybridomas cloned by limiting dilution were grown in 2 liter rolling tissue culture flasks. From these cultures, secreted monoclonal antibodies were precipitated at 50% ammonium sulfate saturation. The precipitates of monoclonal antibodies were then dialyzed and purified by two-step affinity chromatography, using a Protein A-Sepharose column and a SEN bound to ultralinked carboxy bead column, as described above.

Example 1

Figure 2A:
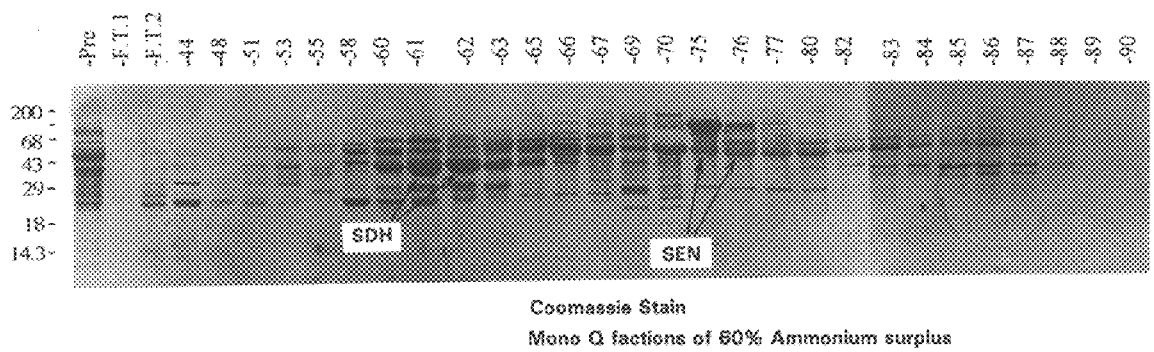
FIGS. 2A–2B. Assay of protein elution fractions from a Mono Q FPLC column.
Figure 2B:
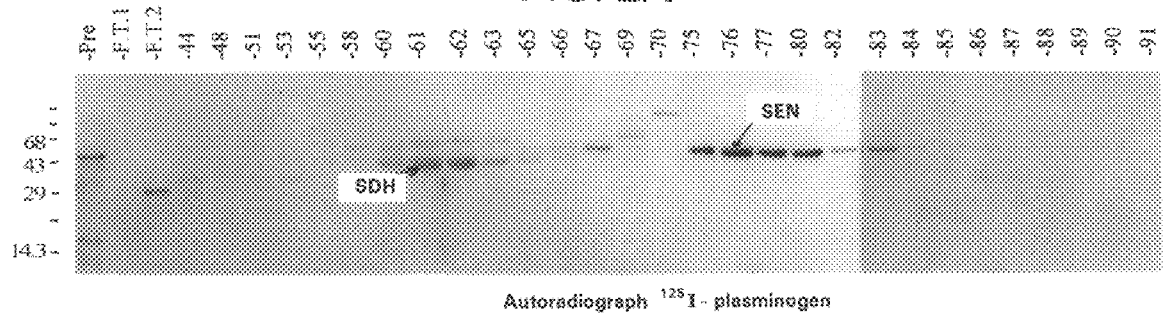

Purification and Characterization of Purified and Membrane-Bound SEN:

Purification of streptococcal surface plasmin binding protein: The dialyzed and concentrated cell wall extracts were sequentially precipitated with ammonium sulfate at 40, 60 and 80% saturation. The precipitated proteins were than dialyzed against 0.05 M Tris/HCl, pH 8.0 and concentrated to an appropriate volume. The proteins in the dialyzed preparations were resolved on to a PVDF membrane and probed with labeled plasmin(ogen). A strong plasmin(ogen) binding activity was found mainly associated with 45 kDa protein. Further, the plasmin(ogen) binding 45 kDa protein was seen only in the preparation that was precipitated at 40 to 60% ammonium sulfate saturation (FIGS. 1 and 2). Thus, for further purification of the 45 kDa plasmin(ogen) binding protein, 40–60% ammonium sulfate precipitation was used as the initial preparation. The dialyzed and concentrated 40–60% precipitates were stored in an aliquot of 10 ml at −70° C. until further use.

A 10-ml aliquot of the dialyzed precipitate was applied to a Mono Q FPLC column (HR10/10, Pharmacia/LKB) equilibrated with 0.05 M Tris/HCl, pH 8.0 buffer. After washing with five column volumes of the starting buffer, bound proteins were eluted with a 70-ml linear NaCl gradient from 0 to 0.7 M and then with 20-ml linear NaCl gradient from 0.7 to 1 M. Protein elution profiles of each fraction was determined by SDS-PAGE and Coomassie blue staining. A duplicate gel was Western blotted and probed with $^{125}$I-plasmin(ogen) as described above (FIG. 2). The 45 kDa plasmin(ogen) binding protein was eluted at a 0.63 M NaCl concentration. The pooled fractions showing the presence of the 45 kDa protein and plasmin(ogen) binding activity were dialyzed against the starting buffer and rechromatographed on the Mono Q column. The fractions that contained the 45 kDA protein were pooled, and then concentrated to a volume of less than one ml, using Centriprep 30 and Centricon 30 concentrators (Amicon). The concentrated sample was then applied to a Superose-12 FPLC column (Pharmacia/LKB) pre-equilibrated with 0.05 M Tris/HCl, pH 8.0 and fractions containing the 45 kDa protein which had plasmin(ogen) binding activity were pooled. These fractions were then concentrated again, and mixed with 4 M ammonium sulfate in a ratio of 1:3, and applied to a Poros BU/M hydrophobic column pre-equilibrated with 0.05 M Tris/HCl, pH 8.0 containing 3 M ammonium sulfate. The protein was eluted by a decreasing linear gradient of 3.0 to 0.0 M ammonium sulfate (20-ml in volume). The 45 kDa protein was eluted in one fraction at 1.32 M ammonium sulfate. The eluted protein was dialyzed and then stored at a concentration of 250 μg/ml at −70° C. until further use.

Figure 4:
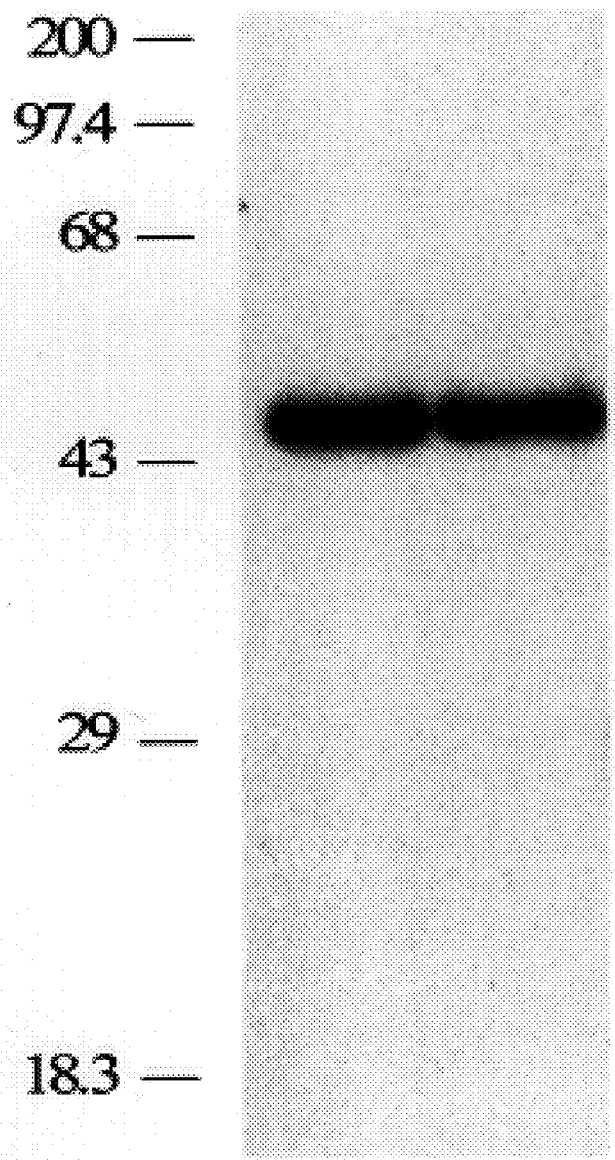
FIG. 4: Resolution of the 45 kDa plasmin binding protein. The plasmin binding protein was resolved by 12% SDS-PAGE under reducing conditions and then further subjected to Western Blot analysis on a PVDF membrane and identified by autoradiography with the use of $^{125}$I-plasminogen as the probe.

N-terminal and internal protein sequencing of the streptococcal surface plasmin(ogen)-binding protein: N-terminal amino acid sequence was determined according to the method described by Matsudaira (Matsudaira, P. (1987) J.Biol.Chem. 262: 10035). The purified 45 kDa protein was resolved on a PVDF membrane by SDS-PAGE and Western blotting. Protein was visualized by staining with 0.1% Ponceau-S (Sigma) in 1% acetic acid. Plasminogen and plasmin binding activity was confirmed by autoradiography (FIG. 4). The section of the membrane containing the protein band was excised, destained with water and subjected to automated Edman degradation (FIG. 4). Each sample contained ~2–3 μg of the protein as determined by the BCA protein method (Pierce Chemical Co, Rockland, Ill. USA). A duplicate sample on a PVDF membrane was digested with lysine specific endopeptidase and the resulting peptide fragments were separated by capillary electrophoresis interphased with MALDI-laser desorption Mass spectrometer (Perseptive Biosystem). Two internal peptide fragments were isolated (peptide-2 having a molecular mass of 1712.1 and peptide-3 having a molecular mass of 3367.1). All microsequence analyses were performed at the Protein/Biotechnology Facility of the Rockefeller University.

Sequence homologies: A portion of the amino acid sequence of the 45 kDa plasmin(ogen) binding protein was determined. The first 50 amino acids at the amino terminus of the protein is shown in FIG. 3. This sequence has more than 90% homology with the N-terminal end of α-enolase. Thus, the plasmin(ogen) binding 45 kDa streptococcal protein was identified and characterized as an α-enolase. This identification was also confirmed by amino terminal sequencing of two internal peptide fragments obtained as described above, (FIG. 3).

Comparison of the amino acid sequences of these two peptides with the published sequences from GenBank allow the confirmation of the identity of the protein as an α-enolase and further predicts that these other two fragments are in the middle of the polypeptide (peptide-2) and towards the C-terminal end of the molecule (peptide-3) respectively.

Enzyme assay and the naming of the protein as SEN: The N-terminal striking sequence homology between the purified 45 kDa protein and α-enolase prompted the investigation as to whether this protein is enzymatically active. Enolase activity was measured both by a coupled assay with NADH, and by a direct assay measuring the change in absorbance at 240 mn due to the conversion of 2-phosphoglycerate to phosphoenolpyruvate.

(a) In a coupled assay, enolase activity was determined by measuring the transformation of NADH+H$^+$ to NAD$^+$ according to the following reactions:

(1)
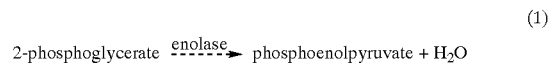

(2)
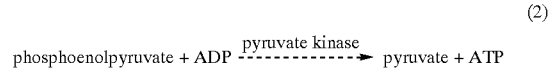

(3)
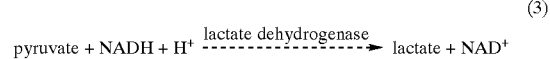

Figure 6:
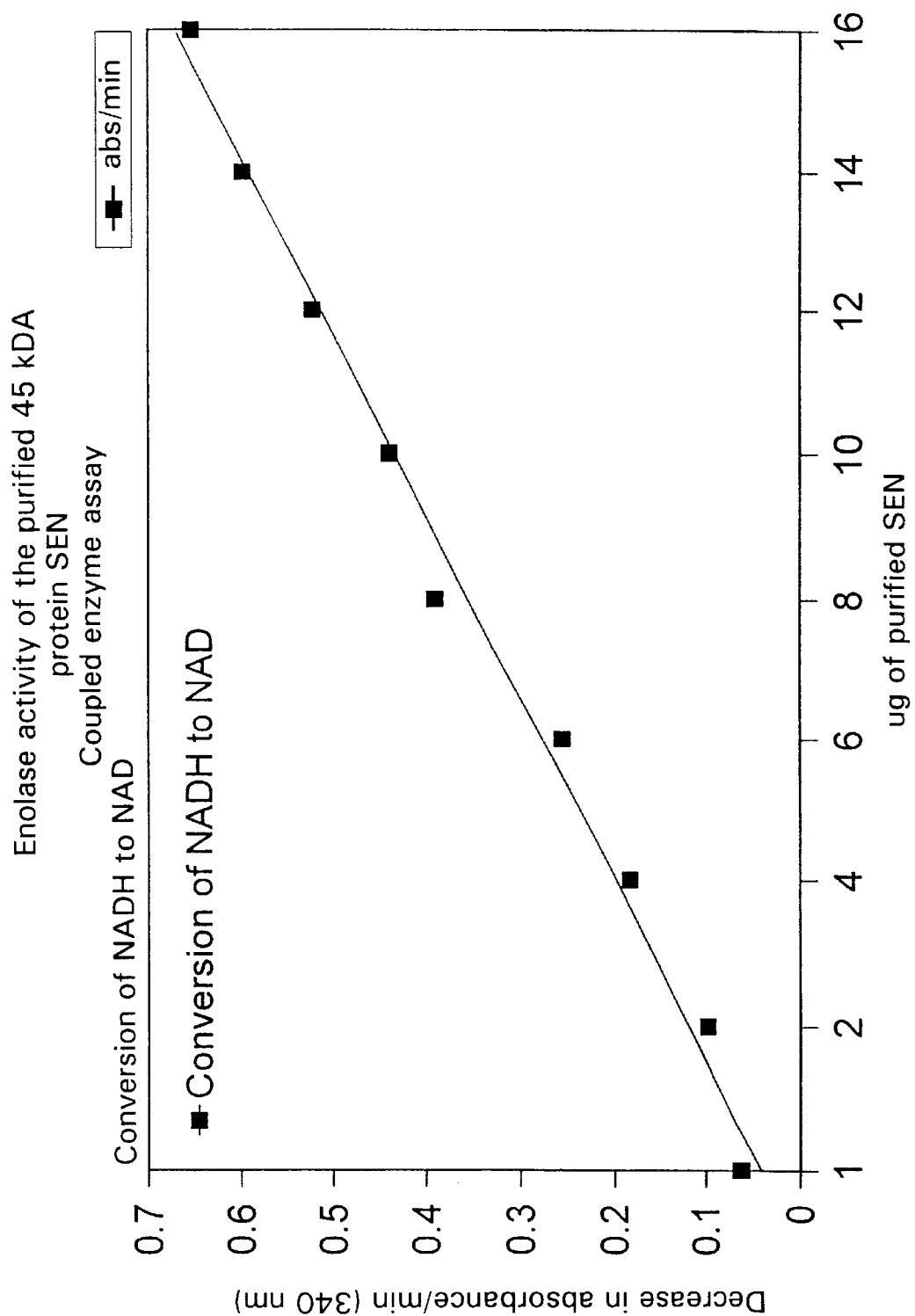
FIG. 6: Enolase activity of the purified plasmin binding protein in the coupled assay. The change in absorbance with time at 340 nm due the conversion of NADH to NAD$^+$ in the coupled assay described in Example 1 as a function of the amount of the purified plasmin binding protein. Conditions as described in Example 1.

The reactions were performed in 1 ml, at 30° C. in 100 mM HEPES buffer, pH 7.0, containing 3.3 mM MgSO$_4$, 0.2 mM NADH, 0.3 mM 2-phosphoglycerate, 1.2 mM ADP, 10.3 IU of lactate dehydrogenase, and 2.7 IU of pyruvate kinase per ml. The reaction was started by adding 100 μl of the test solution. The decrease of the absorbance at 340 nm due to conversion NADH to NAD$^+$, was recorded as the change in absorbance per minute. As the amount of SEN was increased, a corresponding increase in the rate of the reduction in the absorbance at 340 nm was observed (FIG. 6).

Figure 5:
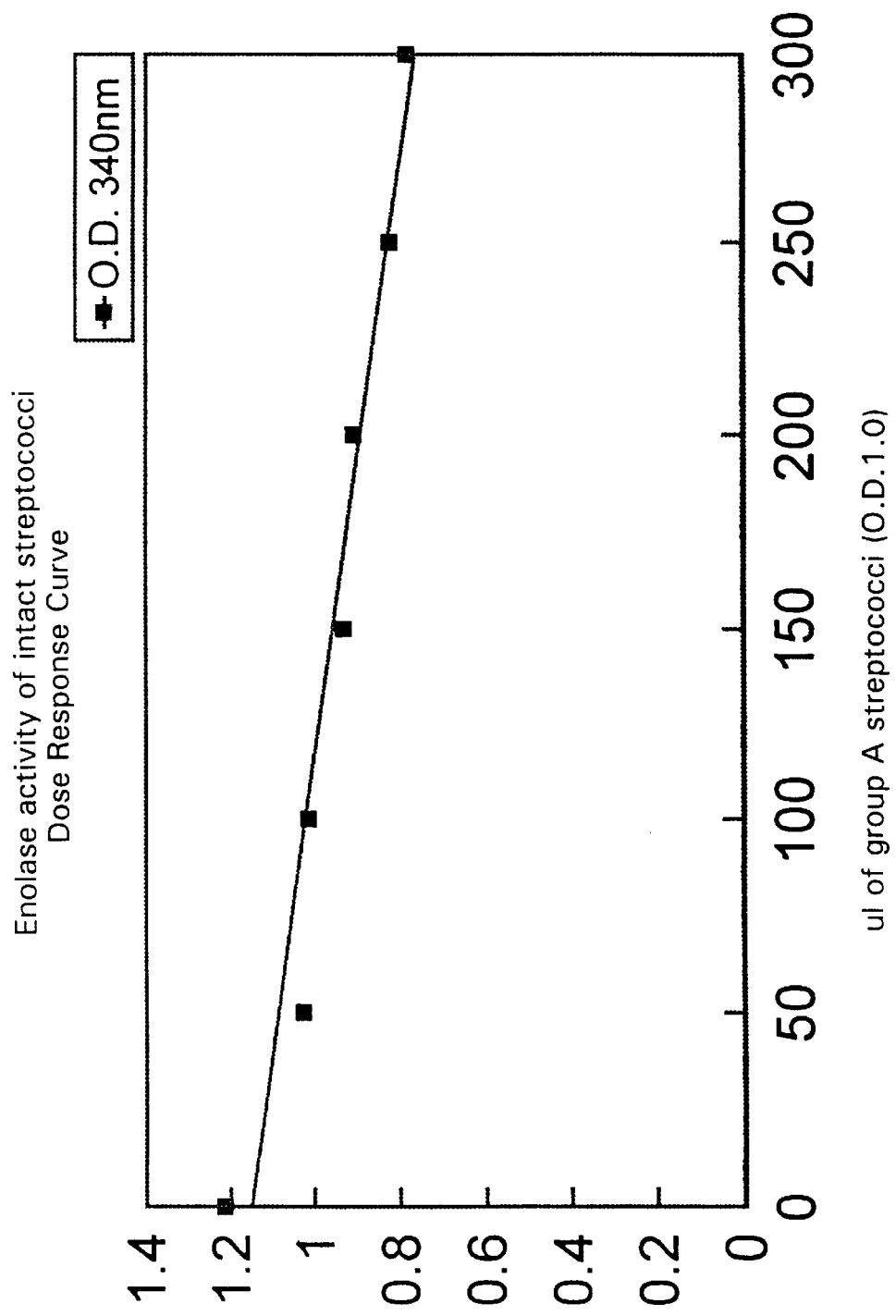
FIG. 5: Enolase activity of intact streptococci: Dose response curve. The change in absolute absorbance at 340 nm due the conversion of NADH to NAD$^+$ in the coupled assay (as described in Example 1) as a function of the concentration of washed, intact group A streptococci. Increases in concentration of the group A streptococci were made by approximately 50 μl increments of a stock solution of group A streptococci.
Figure 7:
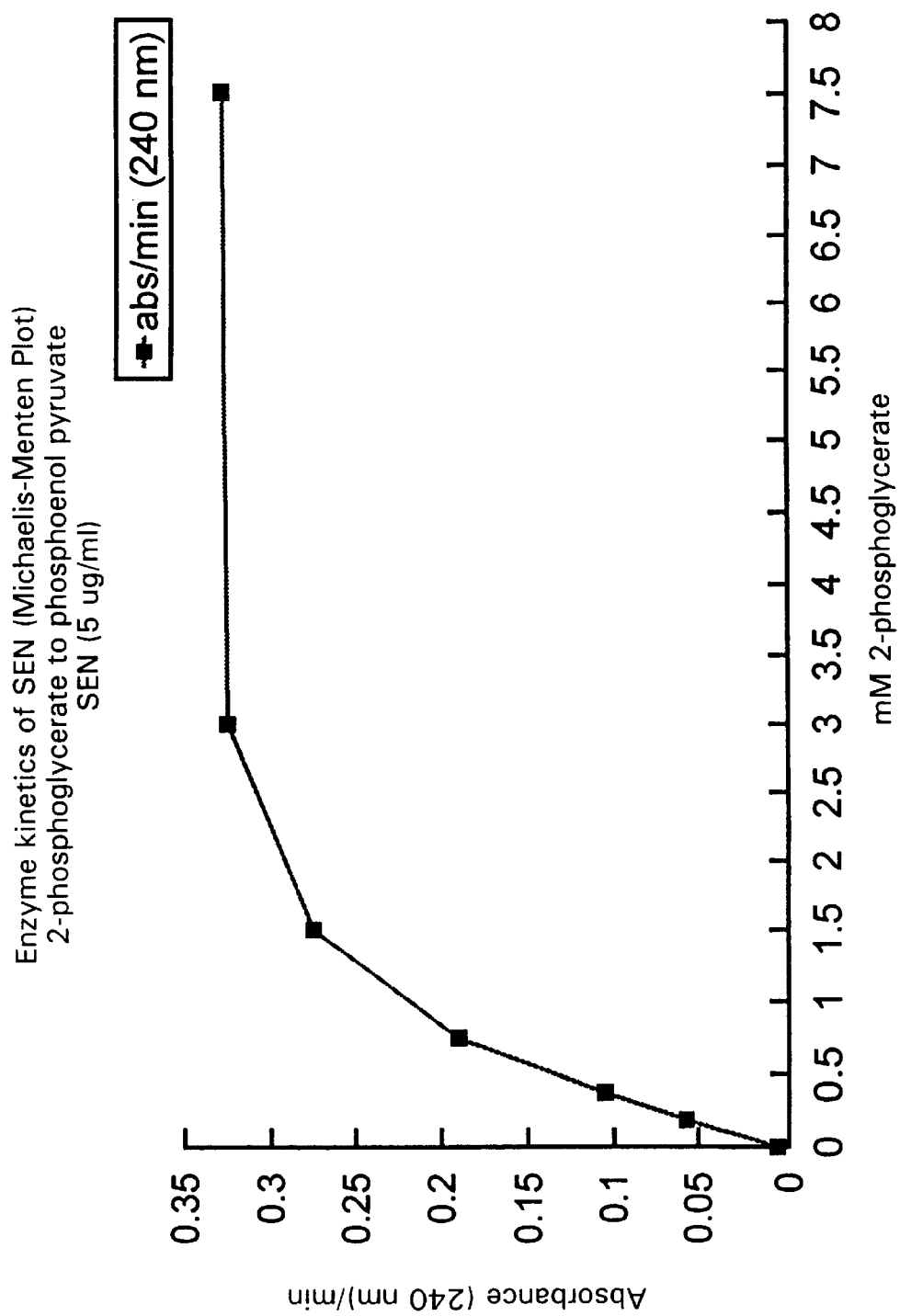
FIG. 7: Michaelis-Menten plot depicting the change in absorbance at 240 nm/minute as a function of the concentration of 2-phosphoglycerate (mM) as catalyzed by the plasmin binding protein. The change in absorbance is due to the conversion of 2-phosphoglycerate to phosphoenolpyruvate. Conditions as described in Example 1.
Figure 8:
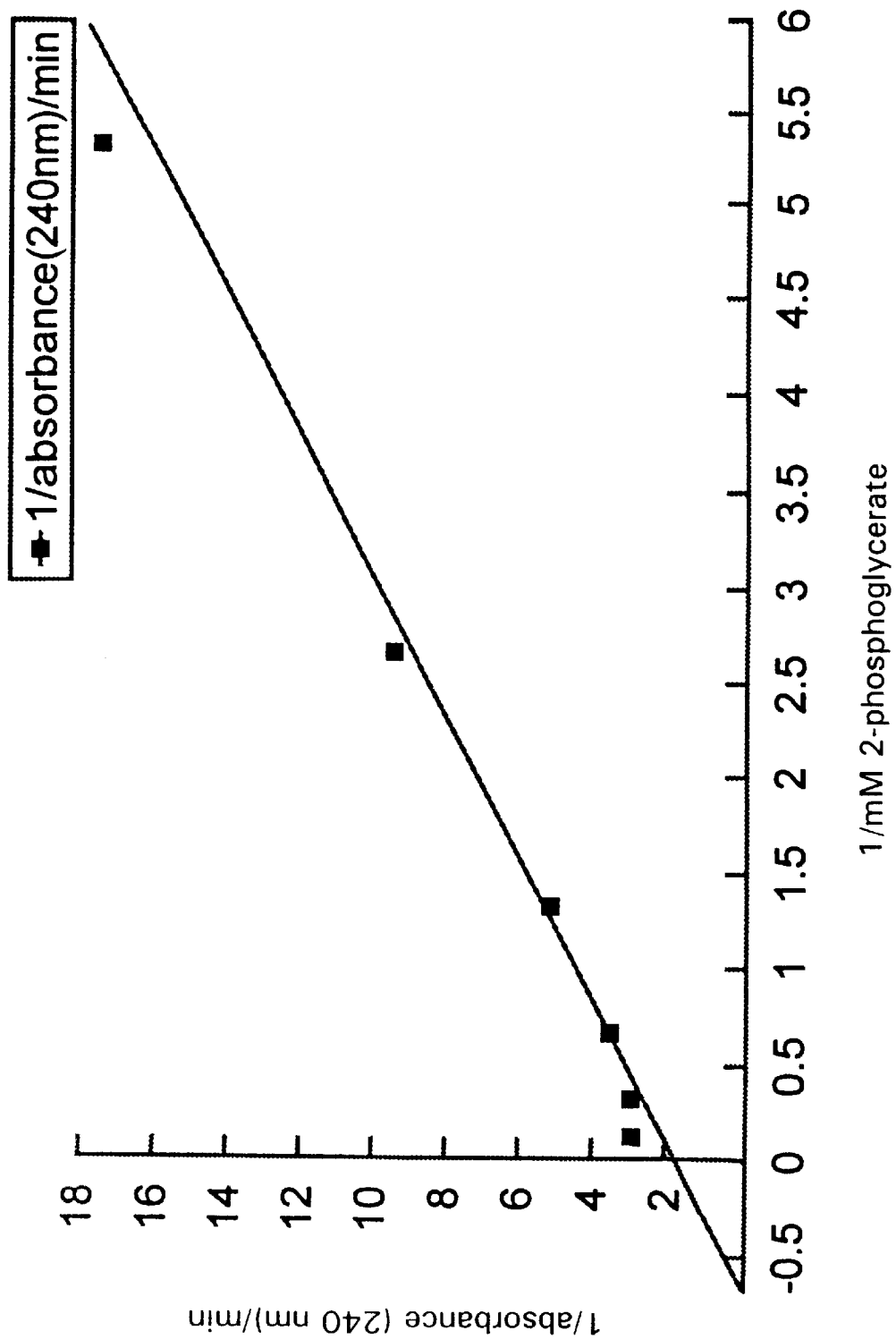
FIG. 8: Double-reciprocal plot depicting the change in the reciprocal of the absorbance at 240 nm/minute as a function of the reciprocal of the concentration of 2-phosphoglycerate (mM) as catalyzed by the plasmin binding protein. The change in absorbance is due to the conversion of 2-phosphoglycerate to phosphoenolpyruvate. Conditions as described in Example 1.

(b) For the kinetic studies, the single enzyme assay was used, involving only the conversion of 2-phosphoglycerate to phosphoenolpyruvate by enolase. This simpler reaction avoids possible interactions of the effectors with the other enzymes. The reaction was performed at 30° C. in 100 mM HEPES buffer, pH 7.0, containing 10 mM MgSO$_4$, 3.2 mM EDTA and 7.7 mM KCl and varying concentrations of 2-phosphoglycerate (0.19–7.5 mM). The change in absorbance/min was monitored at 240 nm. Similar to the coupled enzyme assay, (see above), this assay also revealed a SEN concentration-dependent increase in the enzymatic activity as revealed by the increase in absorbance (FIG. 7). Michaelis-Menten and Lineweaver-Burke plots were drawn from the data obtained using 5 μg of SEN and varying concentrations of 2-phosphoglycerate (FIGS. 7 and 8). From these plots a $V_{max}$ of 270 μmoles phosphoenolpyruvate formed/min-mg SEN and a Km of 1.5 mM for 2-phosphoglycerate was determined (see FIGS. 7 and 8). A concentration-dependent increase in the enolase activity was also found for the intact, washed streptococci (FIG. 5). These data indicated that the 45 kDa plasmin(ogen) binding protein (SEN) is exposed on the surface and is enzymatically active while firmly bound to the surface of outer membrane of streptococci.

Prevalence of SEN in various M types of group A streptococci and streptococcal groups: Proteins from the cell wall extracts of several M serotypes were prepared using lysin enzyme and the mutanolysin extracts of various group strains (gr A, B, C, D, E, F, G, H, L, N) were resolved on SDS-PAGE and transferred to a PVDF membrane (FIG. 9).

The blots were blocked in a blocking buffer containing 0.5% BSA and 0.5% Tween-20, probed with affinity-purified anti-SEN antibodies (1:1000 dil) for 3–4 hours, followed by goat anti-rabbit IgG linked to alkaline phosphatase (1:1000) for 2 hours. The results indicated that SEN is present on the surface of all M types tested (FIG. 9) and all groups except group N.

Example 2

Regulation By $\alpha_2$-Antiplasmin Of The In Vitro Plasmin Activity In The Presence And Absence Of SEN:

In vitro Proteolytic Activity of Plasmin Bound to Intact Streptococci. $\alpha_2$-antiplasmin is a fast-acting plasmin inhibitor found in plasma. Thus the proteolytic activity of plasmin can be evaluated in terms of its inhibition in the presence of $\alpha_2$-antiplasmin. To determine the effect of binding of plasmin to intact streptococci on its proteolytic activity, plasmin (2.5 μg, 50 μl) was first incubated together with intact streptococci ($5 \times 10^7$ bacteria/100 μl) for 1 hour at 37° C. with slow rotations followed by the addition of $\alpha_2$-antiplasmin (0.015 U, 10 μl) for 30 seconds at room temperature. At the end of the reaction, the bacteria were removed by centrifugation and the residual proteolytic activity of plasmin in the supernatants was then measured by determining the ability of bound plasmin to cleave the chromogenic substrate VAL-LEU-LYS-paranitroanilide (Sigma, 25 μg, 50 μl) in a final reaction volume of 200 μl of HBS-gel/TB. The change in absorbance at 405 nm was recorded spectrophotometrically (MR 4000, Dynatech Laboratories, Inc., Chantilly, Va.). Blanks were run with buffer instead of $\alpha_2$-antiplasmin (FIG. 12).

Results showed that plasmin bound to streptococci was not inactivated by $\alpha_2$-antiplasmin and was able to act on a chromogenic substrate as effectively as in the absence of antiplasmin. The control experiment with free plasmin was significantly inactivated in the presence of $\alpha_2$-antiplasmin and showed a minimum activity on a chromogenic substrate (FIG. 12).

Determination of the Functional Consequences of Plasminogen bound to SEN. To study the functional consequences of the binding of plasminogen to Streptococci, kinetic of the activation of plasminogen to its active plasmin form was studied in the presence of streptokinase. The plasminogen activation to plasmin was measured, using the chromogenic substrate. First, the amount of bound $^{125}$I-plasminogen was determined using the fixed number of streptococci ($5 \times 10^7$ bacteria/100 μl) in a 1.5 ml eppendorf tubes after 1 hour of incubation at room temperature, followed by two washings (VBS-gel with tween −20 and 0.5% BSA) to remove free label. An equal amount of free plasminogen was included in the parallel test. Both free plasminogen and streptococci/SEN-linked plasminogen were treated with the fixed amount of streptokinase (20 U/well, 50 μl) in the presence of chromogenic substrate. The rate of activation of plasminogen to plasmin was then determined by measuring the protease activity on the chromogenic substrate as described above. The change in absorbance at 405 nm was recorded as described above.

Figure 12:
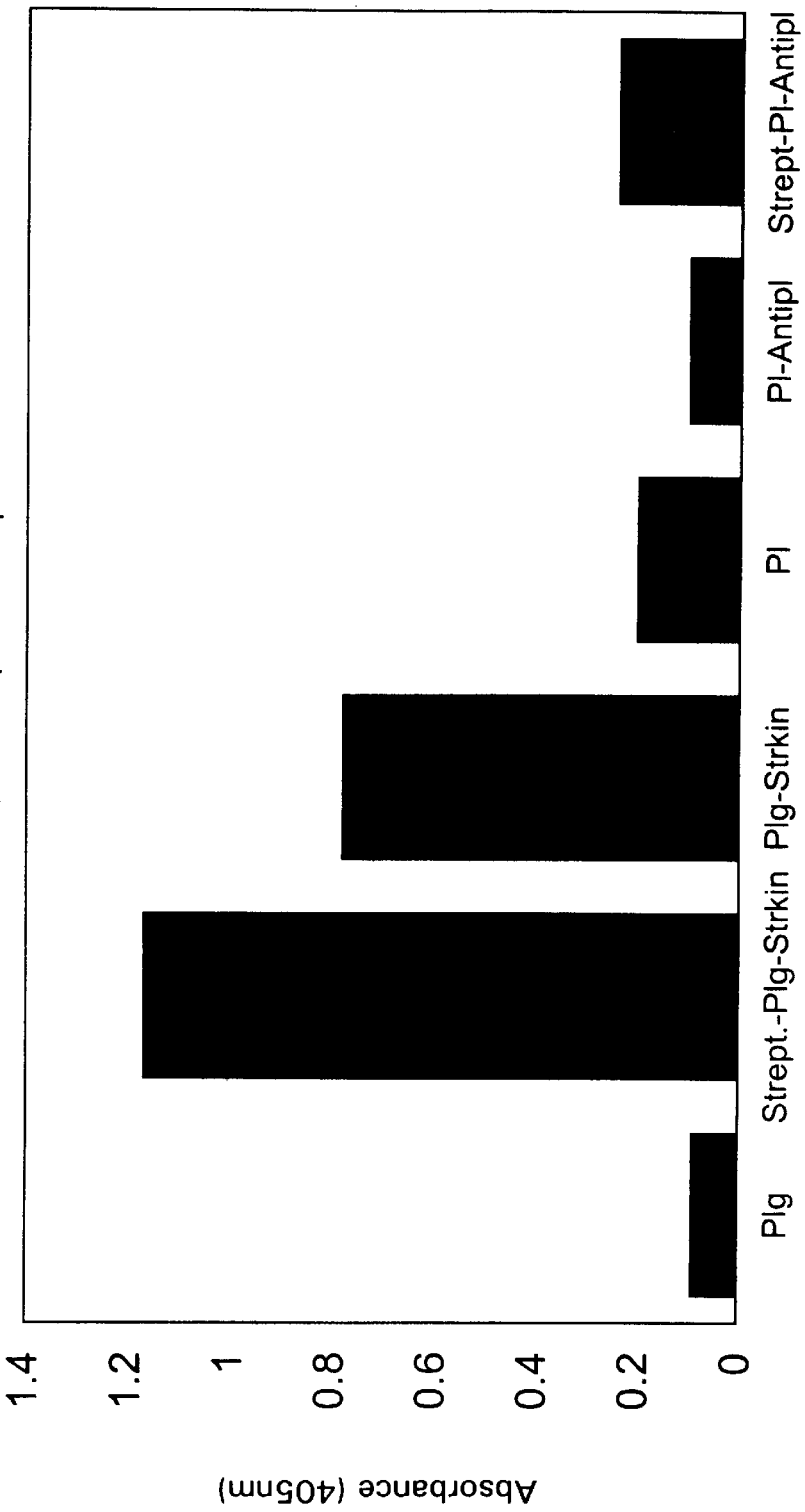
FIG. 12: The effect of the preincubation of plasminogen and plasmin with washed, intact streptococci having SEN on its surface, with respect to their petidase activity after preincubation with streptokinase or $\alpha_2$-antiplasmin respectively. Bar graph depicting the absorbance change at 405 mn due to peptide cleavage of the artificial peptide, D-Val-Leu-Lys p-nitroanilide, by plasmin after pre-incubation of plasmin alone, plasminogen alone or either form of the enzyme with the listed reagents. All samples were assayed as described in Example 2. Free plasminogen (Plg); plasminogen following pre-incubation with streptokinase in the presence of (Strept.-Plg-Strkin); or absence of streptococci (Plg-Strkin); free plasmin (Pl); plasmin that had been preincubated with $\alpha_2$-antiplasmin in the absence of (Pl-Antipl); or presence of streptococci (Strept.-Pl-Antipl).

Results showed that the streptokinase-mediated activation of plasminogen bound to streptococci had significantly higher activity on the chromogenic substrate as compared to the equal amount of free plasminogen indicating that the plasminogen bound to streptococci were more efficiently activated to plasmin by streptokinase than the equal amount of free plasminogen (FIG. 12).

Example 3

Antibodies Against the SEN Protein

Figure 10:
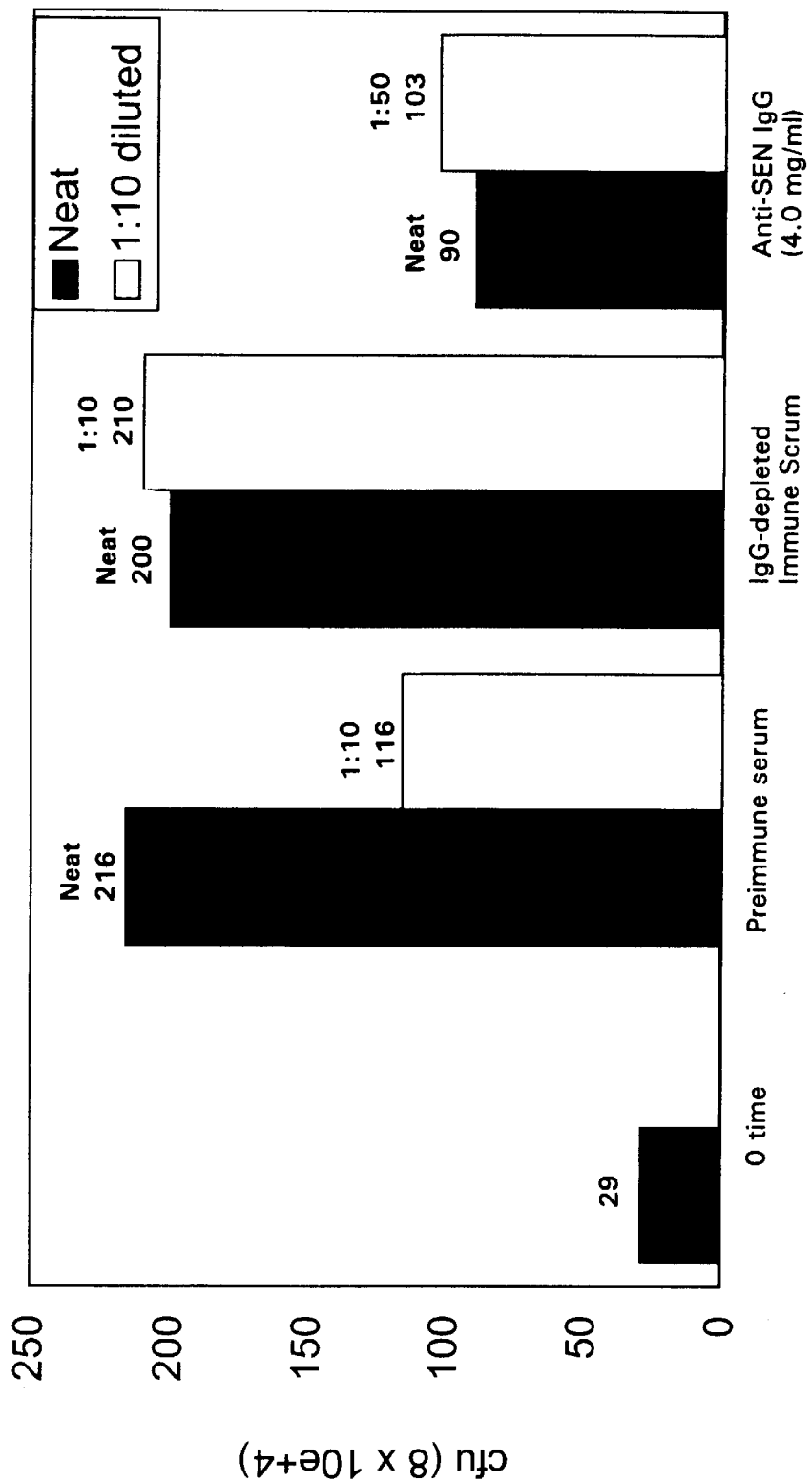
FIG. 10: Phagocytosis of gr. A streptococci (M6): Effect of anti-Sen IgG. Bar graph depicting the in vitro effect of anti-SEN antibodies on *S. pyrogenes* strains survival in the blood of a non-immune individual lacking type-specific antibodies against the type M6 D471 strain bacteria. The surviving bacteria were counted as described in Example 3. The solid bars represent either zero time or the addition of undiluted (Neat) sera or IgG as described in Example 3. The stippled bars represent additions of sera or IgG at the dilutions indicated.

In vitro opsonic activity of anti-SEN antibodies and phagocytosis of group A streptococci: To determine whether SEN-specific antibodies opsonize group A streptococci, rabbit polyclonal anti-SEN antibodies were studied. The opsonic activity of anti-SEN antibodies was measured in terms of the ability of S. pyogenes strains to survive in the blood of a non-imnmune individual lacking type-specific antibodies against the type M6 D471 strain bacteria. Briefly, 0.4 ml of freshly drawn heparinized blood was mixed with 0.1 ml of logarithmic-phase culture of S. pyogenes (100–300 cfu/ml) in the presence of different concentrations of anti-SEN antibodies. These culture mixtures were incubated at 37° C. for 4 hours with constant rotation. The cultures were then plated in Todd-Hewitt (TH) agar and incubated at 37° C. overnight. Surviving bacteria were counted. Both SEN-specific polyclonal sera and affinity purified anti-SEN IgG effectively opsonized and enhanced the phagocytosis of group A streptococci in a dose dependent manner. These in vitro findings indicate that anti-SEN antibodies have a protective role against streptococcal infection. SEN therefore, appears to serve as a virulence factor on the surface of group A streptococci. (FIG. 10)

Example 4

Figure 11:
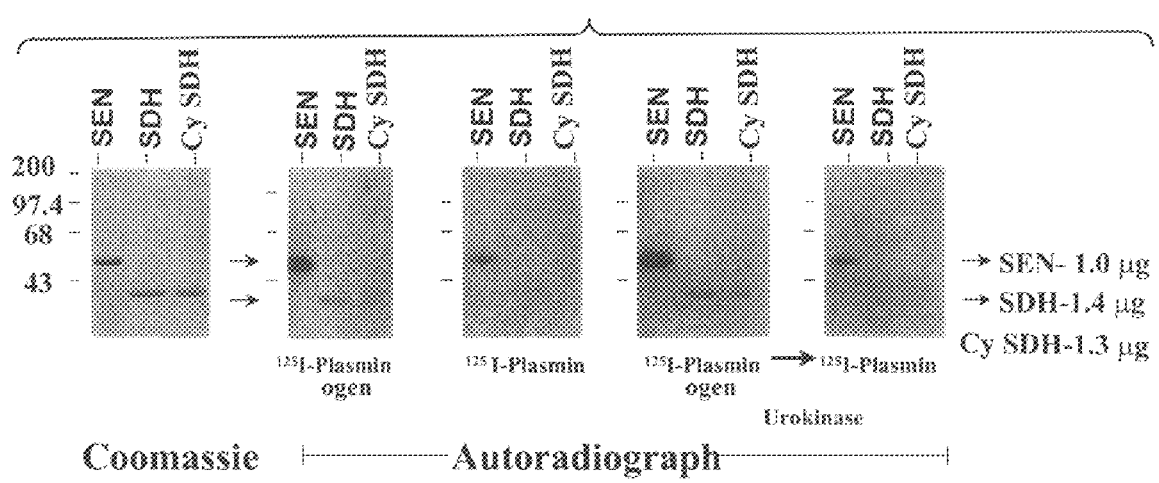
FIG. 11: Comparison between plasmin and/or plasminogen binding activities of SEN and Streptococcal surface dehydrogenase (SDH). An equal amount of purified SEN (1.0 μg), SDH (1.4 μg) and Cyt SDH (1.3 μg), a homolog of SDH that had been purified from the streptococcal cytoplasm, were resolved on a PVDF membrane by 12% SDS-PAGE under reducing conditions, and then Western blotted. Five similar sets of PVDF membranes each containing SEN, SDH, and CytSDH with the above denoted concentrations were obtained. One gel was stained with Coomassie Blue (extreme left hand portion) and the remaining gels were probed by autoradiography with commercially available plasminogen and plasmin that were individually labeled with $^{125}$I as indicated. $^{125}$I-plasmin was also derived from the $^{125}$I-plasminogen by urokinase action, as indicated in Example 4.

Comparison of plasmin binding activity of SEN with that of SDH:

In order to confirm the strong plasmin(ogen) binding activities of SEN as compared to the other previously reported weak plasmin(ogen) binding SDH or a structurally similar Plr protein (Lottenberg et al supra), an equal amount of purified SEN (1.0 μg), SDH (1.4 μg) and a homolog of SDH (Cyt SDH 1.3 μg) purified from the streptococcal cytoplasm were resolved on a PVDF membrane by SDS-PAGE and Western blotting. Five similar sets of PVDF membranes each containing SEN, SDH, and CytSDH with above said concentration were obtained. One set was stained with Coomassie and the remaining were probed with commercially available plasminogen and plasmin that were individually labeled with $^{125}$I. In an another experiment, $I^{125}$-plasmin was derived from the $I^{125}$-plasminogen by urokinase action. In this, at the end of reaction, the cleaved labeled product ($^{125}$I-plasmin) was purified on a PD-10 column and used as probe to examine its ability to bind SEN,SDH or cyt SDH. The results consistently showed as we reported previously that SDH or cytSDH is a weak plasmin(ogen) binding proteins, however, SEN is in fact a strong plasmin(ogen) binding protein (FIG. 11).

The fact that in a crude streptococcal cell wall extract (representing all surface and cell wall-associated proteins) SEN is the protein which showed a majority of the plasmin (ogen) binding activity, as compared to no more than a minimal amount of such binding to SDH, clearly indicates that plasmin(ogen) binding activity of intact streptococci is predominantly if not exclusively due to SEN.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all molecular weight or molecular mass values, given for polypeptides are approximate, and are provided for description.

Various publications are cited herein, the disclosures of which are incorporated by reference in their entireties.

What is claimed is:

1. An isolated polypeptide having the following characteristics:
   (a) it binds to plasmin, wherein said binding impedes the inhibition of the fibrinolytic activity of plasmin by $\alpha_2$-antiplasmin;
   (b) it is isolatable from the surface of a group A streptococcus bacterium;
   (c) it has a molecular weight of 45 kDa determined by SDS-PAGE under reducing conditions; and
   (d) it comprises the N-terminal amino acid sequence of SEQ ID NO: 1.

2. The isolated polypeptide of claim 1 that binds plasminogen.

3. The isolated polypeptide of claim 2 wherein the ability of a plasminogen activator to convert plasminogen to plasmin is enhanced when the isolated polypeptide is bound to plasminogen.

4. The isolated polypeptide of claim 1 that can catalyze the dehydration of D-glycerate-2-phosphate to phosphoenolpyruvate.

5. A composition comprising the isolated polypeptide of claim 1 bound to plasmin.

6. A composition comprising the isolated polypeptide of claim 1 and an anti-fibrin antibody.

7. An immunogenic composition comprising the isolated polypeptide of claim 1 and a pharmaceutically acceptable carrier.

8. The immunogenic composition of claim 7 wherein the isolated polypeptide is attached to a solid phase support.

9. The immunogenic composition of claim 7 further comprising a plasminogen activator.

10. The immunogenic composition of claim 9 wherein the plasminogen activator is tissue plasminogen activator.

11. The immunogenic composition of claim 9 wherein the plasminogen activator is selected from the group consisting of streptokinase, urokinase, and mixtures thereof.

12. An immunogenic composition comprising the composition of claim 5 and a pharmaceutically acceptable carrier.

13. An immunogenic composition comprising the composition of claim 6 and a pharmaceutically acceptable carrier.

14. An immunogenic fragment of an isolated polypeptide, wherein said polypeptide has the following characteristics:
   (a) it binds to plasmin, wherein said binding impedes the inhibition of the fibrinolytic activity of plasmin by $\alpha_2$-antiplasmin;
   (b) it is isolatable from the surface of a group A streptococcus bacterium;
   (c) it has a molecular weight of 45 kDa determined by SDS-PAGE under reducing conditions; and
   (d) it comprises the N-terminal amino acid sequence of SEQ ID NO: 1.

15. An immunogenic composition comprising the isolated polypeptide of claim 1 together with a non-toxic adjuvant.

16. An immunogenic composition comprising the immunogenic fragment of claim 14 together with a non-toxic adjuvant.

17. The immunogenic fragment of claim 14 consisting of the amino acid sequence of SEQ ID NO: 1.

18. A chimeric protein comprising an isolated polypeptide having the following characteristics:
   (a) it binds to plasmin, wherein said binding impedes the inhibition of the fibrinolytic activity of plasmin by $\alpha_2$-antiplasmin;
   (b) it is isolatable from the surface of a group A streptococcus bacterium;
   (c) it has a molecular weight of 45 kDa determined by SDS-PAGE under reducing conditions; and
   (d) it comprises the N-terminal amino acid sequence of SEQ ID NO: 1.

19. The chimeric protein of claim 18 further comprising a fibrin binding domain.

20. The chimeric protein of claim 18 further comprising a catalytic domain from a plasminogen activator.

21. The chimeric protein of claim 18 further comprising the catalytic domain from plasmin.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 50 amino acids
       (B) TYPE: amino acid
       (C) STRANDEDNESS: single
       (D) TOPOLOGY: linear (ii) MOLECULE TYPE: peptide (iii) HYPOTHETICAL: NO (v) FRAGMENT TYPE: internal (vi) ORIGINAL SOURCE:
       (A) ORGANISM: Streptococcus pyogenes (xi) SEQUENCE DESCRIPTION: SEQ ID NO:1:

Ser Ile Ile Thr Asp Val Tyr Ala Arg Glu Val Leu Asp Ser Arg Gly
1               5                   10                  15

Asn Pro Thr Leu Glu Val Glu Val Tyr Thr Glu Ser Gly Ala Phe Gly
            20                  25                  30

Arg Gly Met Val Pro Ser Gly Ala Gly Thr Thr Glu His Glu Ala Val
        35                  40                  45

Glu Leu
    50

(2) INFORMATION FOR SEQ ID NO:2:

(i) SEQUENCE CHARACTERISTICS:
       (A) LENGTH: 48 amino acids
       (B) TYPE: amino acid
       (C) STRANDEDNESS: single
       (D) TOPOLOGY: linear (ii) MOLECULE TYPE: peptide (iii) HYPOTHETICAL: NO (v) FRAGMENT TYPE: internal (vi) ORIGINAL SOURCE:
       (A) ORGANISM: Bacillus subtilis (xi) SEQUENCE DESCRIPTION: SEQ ID NO:2:

Ile Val Asp Val Tyr Ala Arg Glu Val Leu Asp Ser Arg Gly Asn Pro
1               5                   10                  15

Thr Val Glu Val Glu Val Tyr Thr Glu Thr Gly Ala Phe Gly Arg Ala
            20                  25                  30

Leu Val Pro Ser Gly Ala Ser Thr Gly Gln Tyr Glu Ala Val Glu Leu
        35                  40                  45

(2) INFORMATION FOR SEQ ID NO:3:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: peptide

```
    (iii) HYPOTHETICAL: NO (v) FRAGMENT TYPE: internal (vi) ORIGINAL SOURCE:
         (A) ORGANISM: Streptococcus pyogenes (xi) SEQUENCE DESCRIPTION: SEQ ID NO:3:

Glu Arg Gly Leu Val Thr Ala Val Gly Asp Glu Gly Gly Phe Ala
1               5                  10                  15

(2) INFORMATION FOR SEQ ID NO:4:

(i) SEQUENCE CHARACTERISTICS:
         (A) LENGTH: 23 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: Bacillus subtilis (xi) SEQUENCE DESCRIPTION: SEQ ID NO:4:

Val Leu Ser Ala Lys Gly Leu Asn Thr Ala Val Gly Asp Glu Gly Gly
1               5                  10                  15

Phe Ala Pro Asn Leu Gly Ser
            20

(2) INFORMATION FOR SEQ ID NO:5:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: Streptococcus pyogenes (xi) SEQUENCE DESCRIPTION: SEQ ID NO:5:

Ser Ala Ala Gly Tyr Thr Ala Val Val Ser His
1               5                  10

(2) INFORMATION FOR SEQ ID NO:6:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal
```

-continued

```
(vi) ORIGINAL SOURCE:
    (A) ORGANISM: Bacillus subtilis (xi) SEQUENCE DESCRIPTION: SEQ ID NO:6:

Glu Met Ala Lys Arg Ala Gly Tyr Thr Ala Val Ile Ser His Arg Ser
1               5                   10                  15
```